(12) United States Patent
Chen

(10) Patent No.: US 10,975,014 B2
(45) Date of Patent: Apr. 13, 2021

(54) ORGANIC LIGAND AND PREPARATION METHOD THEREOF, QUANTUM DOT STRUCTURE MATERIAL, QUANTUM-DOT-CONTAINING LAYER, AND LIGHT EMITTING DIODE

(71) Applicant: BOE TECHNOLOGY GROUP CO., LTD., Beijing (CN)

(72) Inventor: Zhuo Chen, Beijing (CN)

(73) Assignee: BOE TECHNOLOGY GROUP CO., LTD., Beijing (CN)

(*) Notice: Subject to any disclaimer, the term of this patent is extended or adjusted under 35 U.S.C. 154(b) by 473 days.

(21) Appl. No.: 15/741,756

(22) PCT Filed: Dec. 2, 2016

(86) PCT No.: PCT/CN2016/108360
§ 371 (c)(1),
(2) Date: Jan. 3, 2018

(87) PCT Pub. No.: WO2018/000723
PCT Pub. Date: Jan. 4, 2018

(65) Prior Publication Data
US 2018/0215695 A1  Aug. 2, 2018

(30) Foreign Application Priority Data

Jul. 1, 2016 (CN) .......................... 201610513380.8

(51) Int. Cl.
*C07C 51/15* (2006.01)
*C08G 61/02* (2006.01)
(Continued)

(52) U.S. Cl.
CPC ............... *C07C 51/15* (2013.01); *C07C 1/30* (2013.01); *C07C 51/353* (2013.01); *C07C 57/40* (2013.01);
(Continued)

(58) Field of Classification Search
CPC .......... C07C 51/00; C07C 51/15; C07C 15/20; C07C 15/38
See application file for complete search history.

(56) References Cited

U.S. PATENT DOCUMENTS 3,055,801 A * 9/1962 Torgeson ............. C07D 213/74
514/656
3,255,235 A * 6/1966 Coran ...................... C08K 5/10
560/80
(Continued)

FOREIGN PATENT DOCUMENTS

CN     101200406 A  *  6/2008   ............. C07C 15/56
CN     102617831 A  *  8/2012   ............. G08G 61/02
(Continued)

OTHER PUBLICATIONS

JP 5-194338 (Aug. 3, 1993); machine translation. (Year: 1993).*
(Continued)

*Primary Examiner* — Rip A Lee
(74) *Attorney, Agent, or Firm* — Intellectual Valley Law, P.C.

(57) ABSTRACT

The present disclosure provides quantum dot organic ligand and preparation method thereof, quantum dot structure material, quantum-dot-containing layer, and quantum-dot-containing light emitting diode. The quantum dot organic ligand have the following structure $R_1\text{-}(R_2)_n\text{-}R_3$, wherein $R_1$ is a chelating group capable of chelating with a metal; $R_2$ is a group having a conjugated electron pair, and n is a positive integer; and $R_3$ is organic group. The conjugated electron pair structure of $R_2$ facilitates delocalization of electrons, which can improve the transport and conduction of electrons and/or holes, thereby improving the efficiency of quantum dots and lowering the turn-on voltage.

10 Claims, 4 Drawing Sheets

(51) Int. Cl.
| | |
|---|---|
| H01L 51/50 | (2006.01) |
| C07C 63/44 | (2006.01) |
| C09K 11/02 | (2006.01) |
| C09K 11/88 | (2006.01) |
| C07C 57/40 | (2006.01) |
| C07C 1/30 | (2006.01) |
| C07C 51/353 | (2006.01) |
| B82Y 20/00 | (2011.01) |
| B82Y 40/00 | (2011.01) |

(52) U.S. Cl.
CPC .............. *C07C 63/44* (2013.01); *C08G 61/02* (2013.01); *C09K 11/025* (2013.01); *C09K 11/883* (2013.01); *H01L 51/502* (2013.01); *B82Y 20/00* (2013.01); *B82Y 40/00* (2013.01); *C08G 2261/1412* (2013.01); *C08G 2261/1644* (2013.01); *C08G 2261/3422* (2013.01); *Y10S 977/774* (2013.01); *Y10S 977/815* (2013.01); *Y10S 977/818* (2013.01); *Y10S 977/824* (2013.01); *Y10S 977/892* (2013.01); *Y10S 977/95* (2013.01)

(56) References Cited

U.S. PATENT DOCUMENTS

| | | | | |
|---|---|---|---|---|
| 4,366,079 | A * | 12/1982 | Rauhut | C09B 3/78 |
| | | | | 252/700 |
| 4,696,700 | A * | 9/1987 | Fischer | C09C 1/00 |
| | | | | 106/415 |
| 7,049,012 | B2 * | 5/2006 | Begley | C07C 15/28 |
| | | | | 257/98 |
| 8,860,009 | B2 * | 10/2014 | Ueno | H01L 51/009 |
| | | | | 257/40 |
| 10,287,498 | B2 * | 5/2019 | Zhou | H01L 27/322 |
| 2005/0095452 | A1 * | 5/2005 | Begley | C09K 11/06 |
| | | | | 428/690 |
| 2017/0183567 | A1 | 6/2017 | Zhou et al. | |
| 2018/0215695 | A1 | 8/2018 | Chen | |

FOREIGN PATENT DOCUMENTS

| | | | | |
|---|---|---|---|---|
| CN | 103055954 | A | 4/2013 | |
| CN | 105062462 | * | 11/2015 | |
| CN | 105062462 | A | 11/2015 | |
| CN | 105185918 | A * | 12/2015 | ............ H01L 51/50 |
| CN | 106083573 | A | 11/2016 | |
| CN | 106770137 | A * | 5/2017 | ............ G01N 21/64 |
| FR | 3027532 | A1 * | 4/2016 | ............ B01J 13/22 |
| JP | 5-194338 | A * | 8/1993 | ............ C07C 229/52 |
| JP | 11-273861 | A * | 10/1999 | ............ H05B 33/14 |
| JP | 2008-71863 | A * | 3/2008 | ............ H01L 51/50 |

OTHER PUBLICATIONS

Sasaki, R.; Nako, Y.; Murata, S. Tetrahedron 2009, 65, 7363-7371. (Year: 2009).*
Kano, K.; Ishimura, T.; Hashimoto, S. J. Phys. Chem. 1991,95, 7839-7843. (Year: 1991).*
International Search Report & Written Opinion dated Apr. 11, 2017, regarding PCT/CN2016/108360.
Engineered Chimeric Enzymes as Tools for Drug Discovery: Generating Reliable Bacterial Screens for the Detection, G Skretas et al., Discovery and Assessment of Estrogen Receptor Modulators Journal of the American Chemical Society, No. 27, vol. 129, pp. 8443-8457 (Jun. 15, 2007).
Asymmetric Grignard Cross-Coupling Reaction Using Chiral Ligands Derived from Carbohydrates, A Iida et al., Bulletin of the Chemical Society of Japan, No. 7, vol. 61, pp. 2365-2367 (Jul. 31, 1988).
Regioselective Heck reaction of aliphatic olefins and aryl halides, L Qin et al., Chemical Communication, No. 87, vol. 49, pp. 10236-10238 (Sep. 10, 2013).
Formation of Olefins from Alkyl Radicals with Leaving Groups in the β-Position, Manfred K. Eberhardt, The Journal of Organic Chemistry, No. 20, vol. 49, pp. 3720-3725 (Oct. 30, 1984).
High-Efficiency, Low Turn-on Voltage Blue-Violet Quantum-Dot-Based Light-Emitting Diodes, Huaibin Shen et al., Nano Lett., 2015, 15 (2), pp. 1211-1216.
First Office Action in the Chinese Patent Application No. 201610513380. 8, dated Feb. 24, 2018, English translation attached.
Extended European Search Report in the European Patent Application No. 16889668.6, dated Jan. 20, 2020.
Namhun Kim et al., "Color Temperature Control of Quantum Dot White Light Emitting Diodes by Grafting organic Fuorescent Molecules", Journal of Materials Chemistry C, vol. 2, No. 46, Jan. 1, 2014, pp. 9800-9804, XP055656286, ISSN: 2050-7526, DOI: 10.1039/C4TC01780C.
Matthew Mcdowell et al., "Semiconductor Nanocrystals Hybridized with Functional Ligands: New Composite Materials with Tunable Properties", Materials, vol. 3, No. 1, Jan. 22, 2010, pp. 614-637, XP055584035, DOI: 10.3390/ma3010614.
D.J. Milliron et al, "Electroactive Surfactant Designed to Mediate Electron Transfer Between CdSe Nanocrystals and Organic Semiconductors", Advanced Materials, vol. 15, No. 1, Jan. 3, 2003, pp. 58-61, XP055025813, ISSN: 0935-9648, DOI: 10.1002/adma. 200390011
Avvaru Praveen Kumar et al., "Novel Dithiols as Capping Ligands for CdSe Quantum Dots: Optical Properties and Solar Cell Applications", Journal of Materials Chemistry C, vol. 3, No. 9, Jan. 1, 2015, pp. 1957-1964, XP055656327, ISSN: 2050-7525, DOI: 10.1039/CATC01863J.
Jae Kwan Lee et al., "Organic-Inorganic Nanostructure Architecture via Directly Capping Fullerenes onto Quantum Dots", Nanoscale Research Letters, Dec. 1, 2011, pp. 1-4, XP055656341, New York DOI: 10.1007/s11671-010-9764-1.
Qiqi Li et al., "Nitrogen-Doped Colloidal Graphene Quantum Dots and Their Size-Dependent Electrocatalytic Activity for the Oxygen Reduction Reaction", Journal of the American Chemical Society, vol. 134, No. 46, Nov. 8, 2012, pp. 18932-18935, XP055656135, ISSN: 0002-7863, DOI: 10.1021/ja309270h.
Kamrul Hassan et. al, "[pi]-Expanded Axially Chiral Biaryls and Their Emissions: Molecular Design, Syntheses, Optical Resolution, Absolute Configuration, and Circularly Polarized Luminescence of 1,1'-Bipyrene-2,2'-diols", Chemistry Letters, vol. 44, No. 11, Nov. 5, 2015, pp. 1607-1609, XP055656053, ISSN: 0366-7022, DOI:10. 1246/cl.150704.
IUPAC Gold Book: Chelation In: "IUPAC Compendium of Chemical Terminology", Jun. 12, 2009, IUPAC, Researcah Triangle Park, NC, XP055655890, ISBN:978-0-9678550-9-7 DOI:10.1351/goldbook. C01012.

* cited by examiner

ORGANIC LIGAND AND PREPARATION METHOD THEREOF, QUANTUM DOT STRUCTURE MATERIAL, QUANTUM-DOT-CONTAINING LAYER, AND LIGHT EMITTING DIODE

CROSS-REFERENCES TO RELATED APPLICATIONS

This application is a national stage application under 35 U.S.C. § 371 of International Application No. PCT/CN2016/108360, filed Dec. 2, 2016, which claims the priority of Chinese Patent Application No. 201610513380.8, filed on Jul. 1, 2016, the entire content of which is incorporated herein by reference.

FIELD OF THE DISCLOSURE

The present disclosure generally relates to the field of quantum dot technologies and, more particularly, relates to organic ligands and preparation method thereof, quantum dots, quantum-dot-containing layer, and light emitting diode.

BACKGROUND

With the development of quantum dot preparation technologies, the stability and luminous efficiency of quantum dots (QDs) have been improved. There have been focuses on applying quantum dots to electroluminescent diodes to obtain quantum-dot-based light-emitting diode (QD-LED).

However, there is a need to provide quantum dot (QD) organic ligand and its preparation method, quantum dot structure material, quantum-dot-containing layer, and QD-based LED with improved efficiency and reduced turn-on voltages.

BRIEF SUMMARY OF THE DISCLOSURE

The technical problem to be solved by the present disclosure includes: providing a quantum dot organic ligand; and applying the quantum dot organic ligands to quantum dots (QDs) to form QD structure materials. When these QD structure materials are further applied in quantum-dot-based light emitting diodes (QD-LEDs), the efficiency of the QD-LEDs can be improved and the turn-on voltage (i.e., light-up voltage) of the QD-LEDs can be lowered.

One aspect of the present disclosure provides a quantum dot organic ligand including a structure represented by a formula: R1-(R2)$_n$-R3. Specifically, R1 can be a chelating group capable of chelating with a metal; R2 can be a group having a conjugated electron pair, and n is an integer equal to or greater than 1; and R3 can be an organic group.

In one embodiment, R1 is selected from the group consisting of a phosphine group, a phosphonic acid group, an amino group, a mercapto group, a hydroxyl group, and a combination thereof.

In one embodiment, R2 is a group having at least one benzene ring structure.

In one embodiment, R2 is a group having one benzene ring.

In one embodiment, R2 is a group having two or more benzene rings.

In one embodiment, R2 is a group having a polycyclic aromatic hydrocarbon structure.

In one embodiment. R2 includes a structure selected from the group consisting of: a naphthalene structure, an anthracene structure, a phenanthrene structure, a pyrene structure, and a combination thereof.

In one embodiment, R2 includes at least one of a structure selected from the group consisting of: a fluorene structure, a polythiophene structure, a carbazole structure, a pyrrole structure, an arylamine structure, a derivative structure from any of the aforementioned structures, and a combination thereof; and a structure selected from the group consisting of: a phenazine structure, a quinoline structure, a thiazole structure, a benzimidazole structure, a triazole structure, and a combination thereof.

In one embodiment, R2 includes a structure selected from the group consisting of: a 9,10-Di(2-naphthyl)anthracene structure, a rubrene structure, and a combination thereof.

In one embodiment, R3 is an alkane group.

In one embodiment, the formula representing the quantum dot organic ligand includes Formula (1).

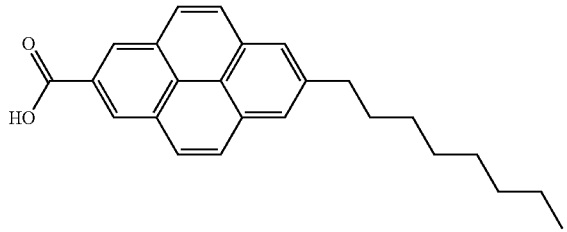

Formula (1)

In one embodiment, the formula representing the quantum dot organic ligand includes Formula (2).

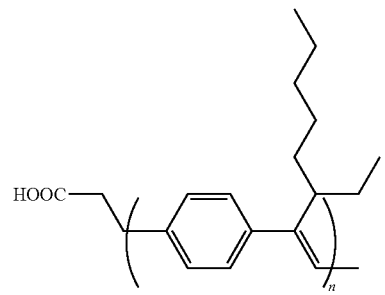

Formula (2)

Another aspect of the present disclosure provides a quantum dot structure. The quantum dot structure includes a shell, a core, and a QD organic ligand.

Another aspect of the present disclosure provides a quantum dot structure. The quantum dot structure includes a structure represented by Formula (3).

Formula (3)

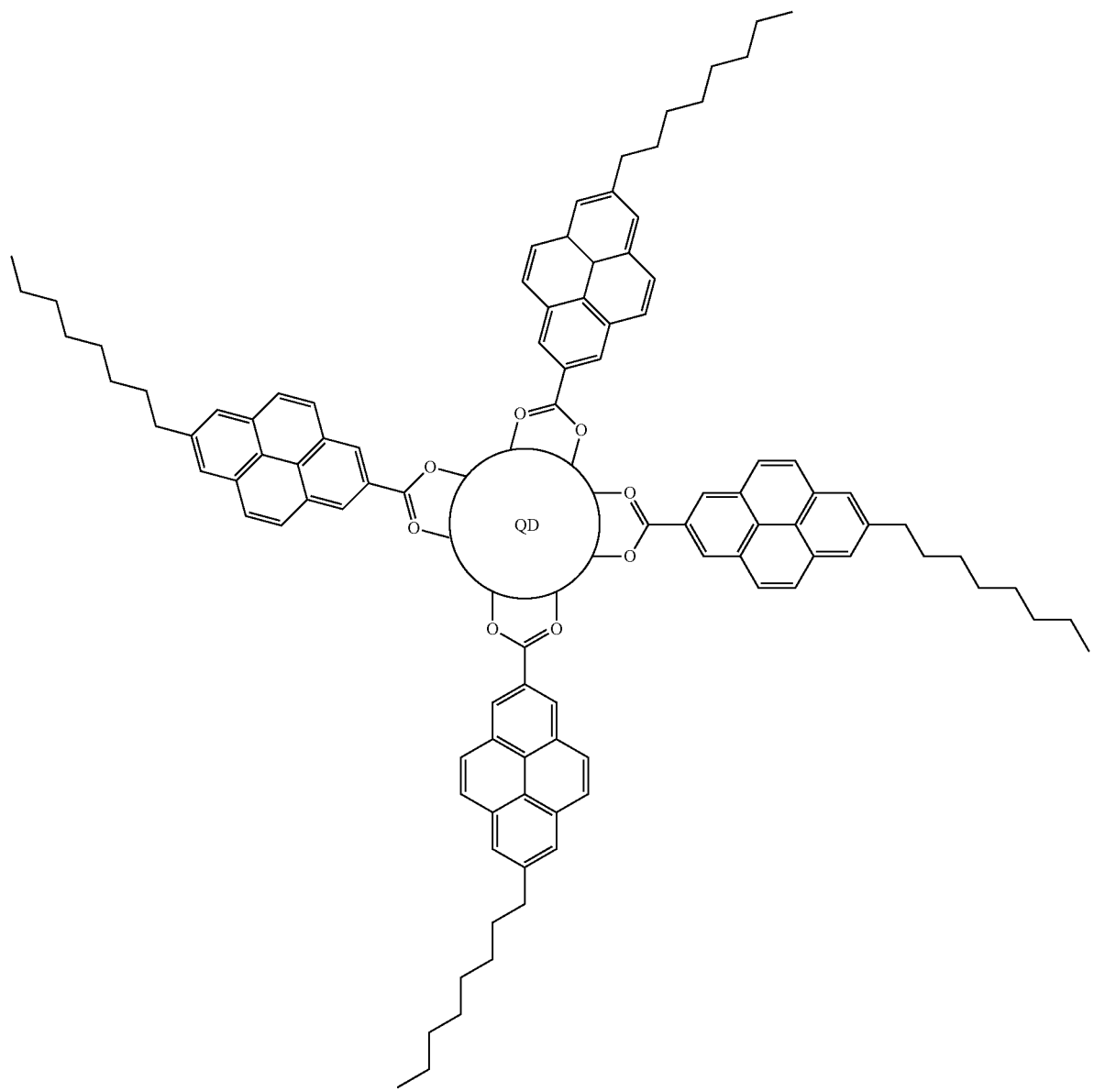

Specifically, QD is an inorganic part of the quantum dot structure, and has a core structure or a core-shell structure. The organic ligands with a structural formula as Formula (1) are configured to chelate on the surface of the QD. Through a carboxyl group of the organic ligand with a structure represented by Formula (1), a chelate linkage is formed between a shell of the core-shell structure of the quantum dot and the quantum dot organic ligand.

In one embodiment, the core-shell structure is made of one or more materials selected from CdS, CdSe, CdTe, ZnSe, InP, PbS, $CsPbCl_3$, $CsPbBr_3$, $CsPhI_3$, $CsPbCl_xBr_{3-x}$, $CsPbBr_xI_{3-x}$, CdS/ZnS, CdSe/ZnS, ZnSe, InP/ZnS, PbS/ZnS, $CsPbCl/ZnS$, $CsPbBr_3/ZnS$, $CsPhI_3/ZnS$, $CsPbClxBr_{3-x}/ZnS$, $CsPbBrxl_{3-x}/ZnS$, and a combination thereof, where $x<3$.

Another aspect of the present disclosure provides a quantum dot structure. The quantum dot structure includes a structure represented by Formula (4).

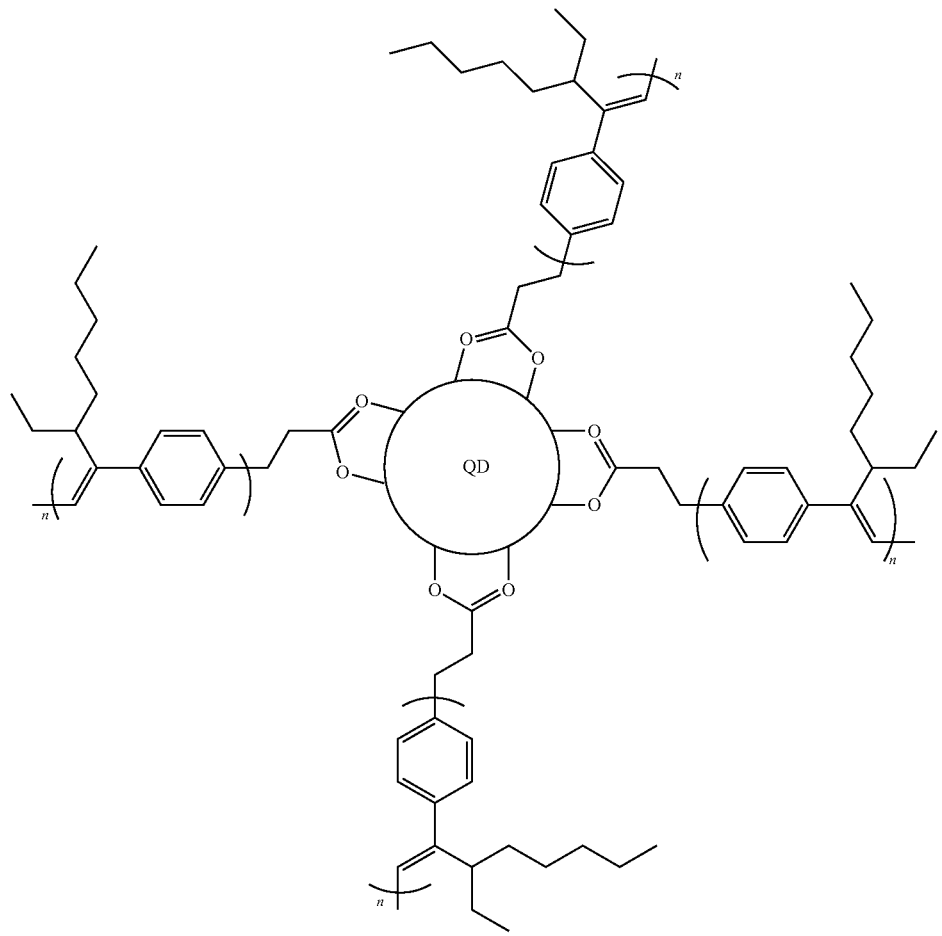

Formula (4)

Specifically, QD represents an inorganic part of the quantum dot structure, and has a core structure or a core-shell structure. The organic ligands with a structure represented by Formula (2) are configured to chelate on the surface of the QD. Through the carboxyl group of the organic ligand with a structure represented by Formula (2), a chelate linkage is formed between a shell of the core-shell structure of the QD and the quantum dot organic ligand.

In one embodiment, the core-shell structure is made of one or more materials selected from CdS, CdSe, CdTe, ZnSe, InP, PbS, $CsPbCl_3$, $CsPbBr_3$, $CsPhI_3$, $CsPbCl_xBr_{3-x}$, $CsPbBr_xI_{3-x}$, CdS/ZnS, CdSe/ZnS, ZnSe, InP/ZnS, PbS/ZnS, $CsPbCl_3$/ZnS, $CsPbBr_3$/ZnS, $CsPhI_3$/ZnS, $CsPbClxBr_{3-x}$/ZnS, $CsPbBrxI_{3-x}$/ZnS, and a combination thereof, where x is a positive integer and x<3.

Another aspect of the present disclosure provides a quantum-dot-containing layer. The quantum-dot-containing layer includes the aforementioned quantum dot structure materials.

Another aspect of the present disclosure provides a quantum-dot-based light emitting diode (QD-LED). The QD-LED includes the aforementioned quantum-dot-containing layer.

Another aspect of the present disclosure provides a method for preparing a quantum dot organic ligand, including: a) producing a $(R2)_n$-R3 compound by a reaction between a $(R2)_n$-Br compound and a R3-Br compound, where R2 is a group having a conjugated electron pair, n is an integer equal to or greater than 1, and R3 is an organic group; b) producing a Br—$(R2)n$-R3 compound by a reaction between the $(R2)_n$-R3 compound and a brominating reagent; and c) producing a R1-$(R2)_n$-R3 compound by a reaction between the Br—$(R2)_n$-R3 compound and a Grignard reagent having R1 group for a Grignard reaction, where R1 is a chelating group capable of chelating with a metal.

Another aspect of the present disclosure provides a method for preparing a quantum dot organic ligand, including: 1) dehydrobrominating 3-(bromomethyl)heptane to produce 3-ethyl-1-octene; and 2) dissolving the 3-ethyl-1-octene, dibromobenzene, 3-(3-Bromophenyl)propionic acid, and a catalyst in an organic solvent to obtain a solution, heating the solution in an inert gas atmosphere for a Heck reaction to produce a polymer having a formula:

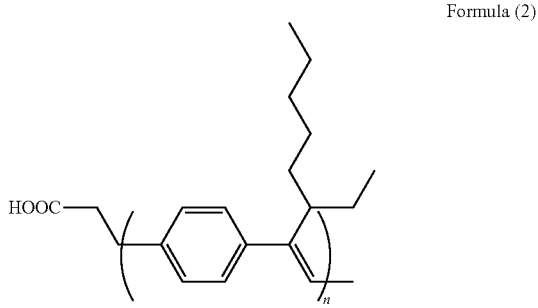

Formula (2)

where n is an integer greater than 1.

The QD organic ligands according to various embodiments of the present disclosure include conjugated electron pair structure that facilitates delocalization of electrons, which facilitates the transport and conduction of electrons and/or holes, thereby improving the efficiency of QD-LEDs and lowering the turn-on voltage of the device.

BRIEF DESCRIPTION OF THE DRAWINGS

The following drawings are merely examples for illustrative purposes according to various disclosed embodiments and are not intended to limit the scope of the present disclosure.

DETAILED DESCRIPTION

Figure 1:
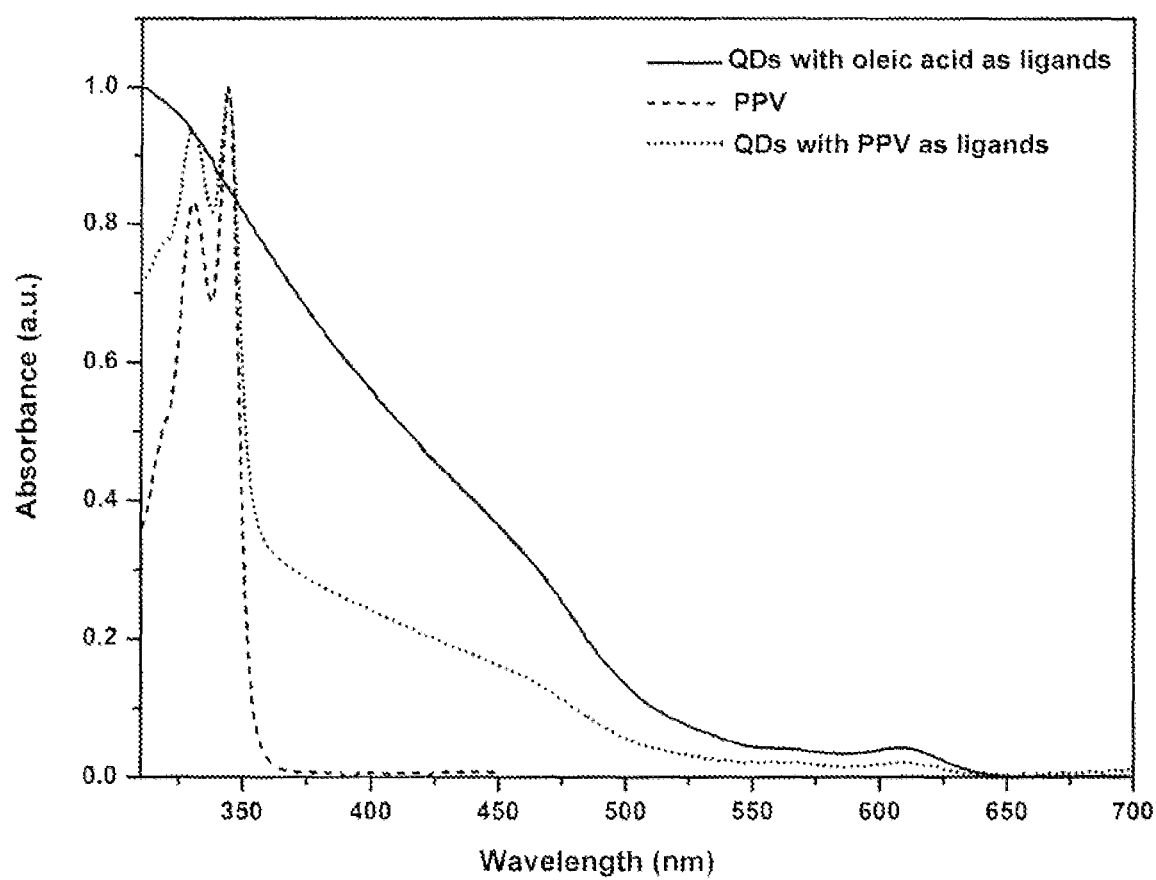
FIG. 1 is a comparison chart illustrating UV-visible light absorbance spectra of: CdTe QDs with oleic acid as ligands prepared according to step 3 of Example 7, QDs with a structural formula as Formula (4) prepared according to step 5 of Example 7, and QD organic ligands prepared according to Example 5.

Reference will now be made in detail to exemplary embodiments of the disclosure, which are illustrated in the accompanying drawings. Hereinafter, embodiments according to the disclosure will be described with reference to the drawings. Wherever possible, the same reference numbers will be used throughout the drawings to refer to the same or like parts. It is apparent that the described embodiments are some but not all of the embodiments of the present disclosure. Based on the disclosed embodiments, persons of ordinary skill in the art may derive other embodiments according to the present disclosure, all of which are within the scope of the present disclosure.

Because of photoluminescence capabilities, quantum dots may be used in light emitting layers in light emitting diodes. Specifically, the structure of a quantum dot may include three parts, i.e., a core, a shell, and/or one or more organic ligands bonded to the core-shell structure through a chelate or other bonding manners. The core-shell provides photoluminescence properties for the quantum dot. The organic ligands can, on one hand, stabilize the core-shell structure and, on the other hand, enhance the ability of the core-shell structure to be dissolved or dispersed in organic solvents.

The molecular structures of the organic ligands usually include a chelating group and an organic chain attached to the chelating group. However, when the organic chain and the quantum dots are contained in a light-emitting layer, the long organic chain may affect the photoluminescence properties of the core-shell structure of the quantum dots, which leads to reduced efficiency of the QD-LED and high turn-on voltages.

As such, the organic chain with reduced length may be used to increase the efficiency of QD-LED and to lower the turn-on voltages of the QD-LED.

The present disclosure provides a quantum dot organic ligand. The quantum dot organic ligand may also be referred to as, ligand, organic ligand, and/or QD organic ligand. The disclosed quantum dot organic ligands are applied to quantum dots (QDs) to form QD structure materials, and when these QD structure materials are further applied in quantum-dot-based light emitting diodes (QD-LEDs), the efficiency of the QD-LEDs can be improved and the turn-on voltage (i.e., light-up voltage) of the QD-LEDs can be lowered.

The detailed embodiments are explained as follows.

A first aspect of the present disclosure provides a quantum dot organic ligand with the following structure:

R1-(R2)$_n$-R3 where R1 can be a chelating group capable of chelating with a metal; R2 can be a group having a conjugated electron pair, where n is an integer equal to or greater than 1; and R3 can be an organic group.

R1 is a chelating group capable of chelating with metal(s). The main role of R1 is to provide chelating ability, so that the QD organic ligand can be anchored to the QD core-shell. R1 may be, for example, a phosphine group, a phosphonic acid group, an amino group, a mercapto group, a hydroxyl group, etc. In one embodiment, R1 is a phosphine group or a phosphonic acid group. It should be noted that, the QD core-shell in the present disclosure can be formed with materials including, but not limited to: CdS, CdSe, CdTe, ZnSe, InP, PbS, CsPbCl$_3$, CsPbBr$_3$, CsPhI$_3$, CsPbCl$_x$Br$_{3-x}$, CsPbBr$_x$I$_{3-x}$, CdS/ZnS, CdSe/ZnS, ZnSe, InP/ZnS, PbS/ZnS, CsPhCl$_3$/ZnS, CsPbBr$_3$/ZnS, CsPhI$_3$/ZnS, CsPbClxBr$_{3-x}$/ZnS, CsPbBrxl$_{3-x}$/ZnS, and combination(s) thereof, where x is a positive integer and x<3.

R2 is a group having a conjugated electron pair, and n is an integer equal to or greater than 1. Due to presence of the conjugated electron pair in the R2 group, desirable organic ligand can be prepared. There is no particular restriction on R2, as long as it is a group containing one or more conjugated electron pairs, such as a conjugated diene, a benzene ring, a conjugated structure of a benzene ring and a double bond olefin, etc.

In one embodiment, R2 is a group with benzene ring structure. R2 can include one benzene ring structure, or two or more benzene ring structures. Alternatively, the R2 group can be a group having a condensed-ring aromatic hydrocarbon structure. The group having one benzene ring structure may be, for example, a benzene structure, a toluene structure, an ethylbenzene structure, etc. The group having two or more benzene ring structures may be, for example, biphenyl, terphenyl, or biphenyl or terphenyl having atom(s) substituted by alkyl. In addition to the structure using a single bond to bond multiple benzene rings, R2 can be a group having a condensed-ring aromatic hydrocarbon structure, such as, a naphthalene structure, an anthracene structure, a phenanthrene structure, and a pyrene structure.

In addition to the groups described above, there are many groups having conjugated electron pair(s) that can be used as R2. For example, in some embodiments, the R2 group can be selected from: a fluorene structure, a polythiophene structure, a carbazole structure, a pyrrole structure, and an arylamine structure, and a derivative structure from any of the aforementioned structures. These structures have hole-transporting capabilities, and can improve the hole injection of the quantum dots.

In one embodiment, R2 can include at least one structure selected from the following group: phenazine structure, quinoline structure, thiazole structure, benzimidazole structure, and triazole structure. The phenazine structure, quinoline structure, thiazole structure, benzimidazole structure, and triazole structure all have electron transport capabilities, and can improve the electronic injection of quantum dots.

R2 can include other organic structures that have electron transport capabilities, for example, condensed ring structures like anthracene and naphthalene. In one embodiment, R2 can include a structure having a luminescence function itself, such as a 9,10-Di(2-naphthyl)anthracene structure and/or a rubrene structure. Further, R2 can include conjugated small molecule having a self-luminous structure, such as 4,4'-Bis(2,2-diphenylvinyl)-1,1'-biphenyl (i.e., DPVBi).

R3 is an alkane group, which serves to improve the dissolving and dispersion of quantum dots in the solvents. The selection of the alkane group is not limited, and R3 can be a long-chain alkane group having more than 4 carbon atoms, or a short-chain alkane group having 4 or less carbon atoms.

Selecting a long-chain alkane group as R3 may assist the dissolving and dispersion of quantum dots in the solvents. Accordingly, in one embodiment, R3 can be a long-chain alkane group. However, when the alkane chain has more than 12 carbon atoms, the solubility of the alkane chain in organic solvents may be reduced. Accordingly, in one embodiment, R3 can be an alkane group having carbon atoms ranging from 5 to 12. Examples of alkane groups having carbon atoms ranging from 5 to 12 may include: pentyl, hexyl, heptyl, octyl, nonyl, decyl, undecyl, dodecyl, etc.

In another embodiment, R3 can be a short-chain alkane group having 4 or less carbon atoms, i.e., C1 to C4 alkane group, such as methyl, ethyl, n-propyl, isopropyl, n-butyl, sec-butyl, tert-butyl, etc.

In the structural formula of the disclosed QD organic ligands, when n is 1, the corresponding QD organic ligand can be regarded as a small molecular organic ligand; when n is an integer greater than 1, particularly when n is an integer of 10 or more, the corresponding QD organic ligand can be considered as a macromolecular type organic ligand, even a polymer type organic ligand.

In one embodiment, n is 1, and the disclosed QD organic ligand has a structural formula as Formula (1).

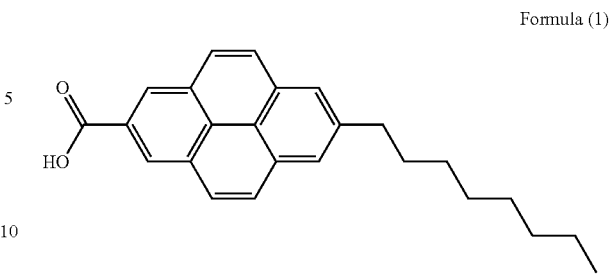

Formula (1)

In this embodiment, R1 is a carboxyl group, R2 has a pyrene structure, and R3 is an octyl group. The pyrene structure includes four conjugated benzene ring structures, the electron cloud distribution is more uniform, and the delocalization effect is more likely to occur. Thus, the pyrene structure is selected to be R2 in this embodiment.

In another embodiment, n is an integer greater than 1, and the disclosed QD organic ligand has a structural formula as Formula (2).

Formula (2)

When n is an integer greater than 1, particularly when n is an integer of 10 or more, the corresponding quantum dot organic ligand has a macromolecular structure or a polymer structure. In the present disclosure, n may be an integer greater than 1. In one embodiment, n is greater than 5. In another embodiment, n is greater than 10. In another embodiment, n is greater than 15. In another embodiment, n is greater than 20. In another embodiment, n is greater than 30.

Quantum dots, quantum-dot-containing layer, or QD-LED prepared using the QD organic ligands according to the first aspect of the present disclosure can achieve higher efficiency and lower turn-on voltage. Specifically, the QD organic ligands according to the first aspect of the present disclosure include conjugated electron pair structure that facilitates delocalization of electrons, which facilitates transport and conduction of electrons and/or holes, thereby improving the efficiency and lowering the turn-on voltage.

The quantum dot efficiency, as used herein, may include external quantum efficiency, current efficiency, and power. In various embodiments according to the first aspect of the present disclosure, the structure of quantum dot organic ligands may be selected according to a perspective of improving the efficiency of quantum dots.

A second aspect of the present disclosure provides a quantum dot structure. The quantum dot structure includes a shell, a core, and a QD organic ligand according to the first aspect of the present disclosure. The core and the shell, as used herein, may be referred to as QD core-shell, or QD core-shell structure, or core-shell structure. The QD core-shell may be one of the aforementioned quantum dot core-shell structures made of CdS, CdSe, CdTe, ZnSe, InP, PbS, $CsPbCl_3$, $CsPbBr_3$, $CsPhI_3$, $CsPbCl_xBr_{3-x}$, $CsPbBr_xI_{3-x}$, CdS/ZnS, CdSe/ZnS, ZnSe, InP/ZnS, PbS/ZnS, $CsPbCl_3$/ZnS, $CsPbBr_3$/ZnS, $CsPhI_3$/ZnS, $CsPbClxBr_{3-x}$/ZnS, $CsPhBrxI_{3-x}$/ZnS, and combination(s) thereof, where x is a positive integer and x<3.

The method of preparing quantum dot structure materials by combining the QD core-shell and the QD organic ligand according to the first aspect of the present disclosure is not particularly limited. Any known method in the art may be applied, such as a direct method, a ligand substitution method. Certain implementations may be provided in the following disclosed embodiments.

A third aspect of the present disclosure provides a quantum dot structure. The quantum dot structure has a structural formula as Formula (3).

Specifically, QD represents an inorganic part of the quantum dot structure, i.e., a quantum dot core structure or a core-shell structure. The organic ligands with a structural formula as Formula (1) are chelated on the QD. Through a carboxyl group of the organic ligand with a structure represented by Formula (1), the shell of the core-shell structure of the quantum dot and the organic ligand form a chelate linkage. Those skilled in the art can understand that the quantum dot structure materials according to the third aspect of the present disclosure are a detailed embodiment according to the second aspect of the present disclosure.

In the structure shown in Formula (3), the connection between the oxygen atoms of the organic ligands and a surface of the QD, shown as a surrounding circle, is represented by a covalent single bond connection. However, in some embodiments, such connection may be explained as having a complex connection mode.

A fourth aspect of the present disclosure provides a quantum dot structure. The quantum dot structure has a structural formula as Formula (4).

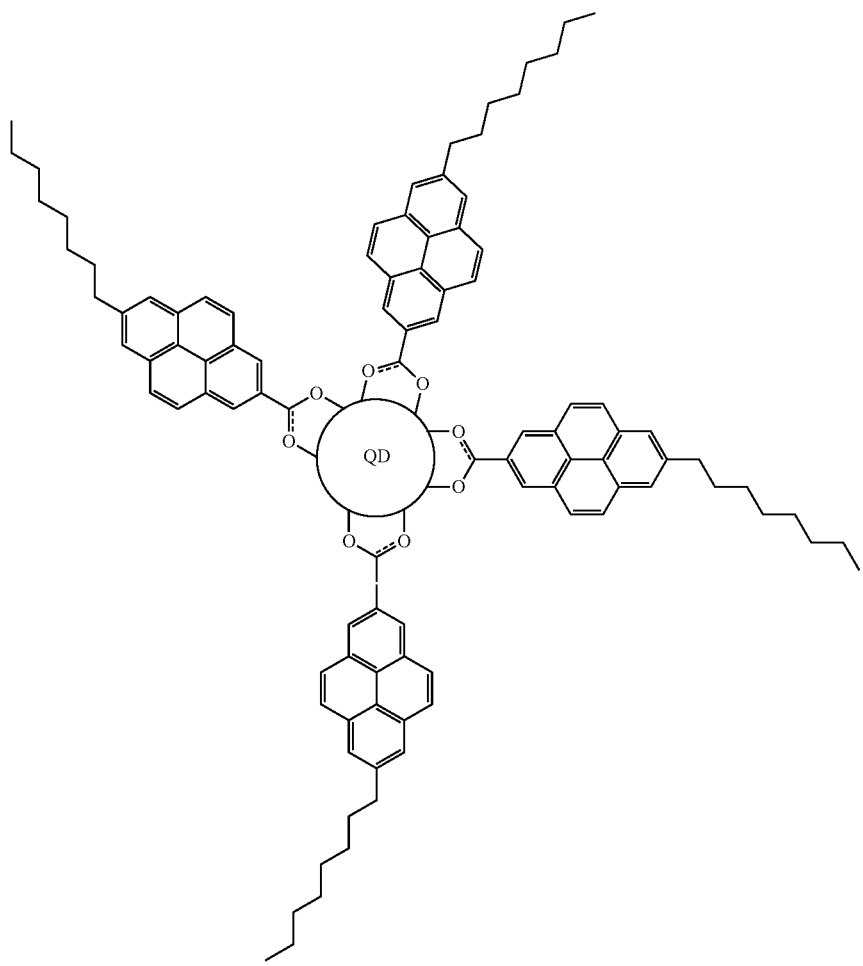

Formula (3)

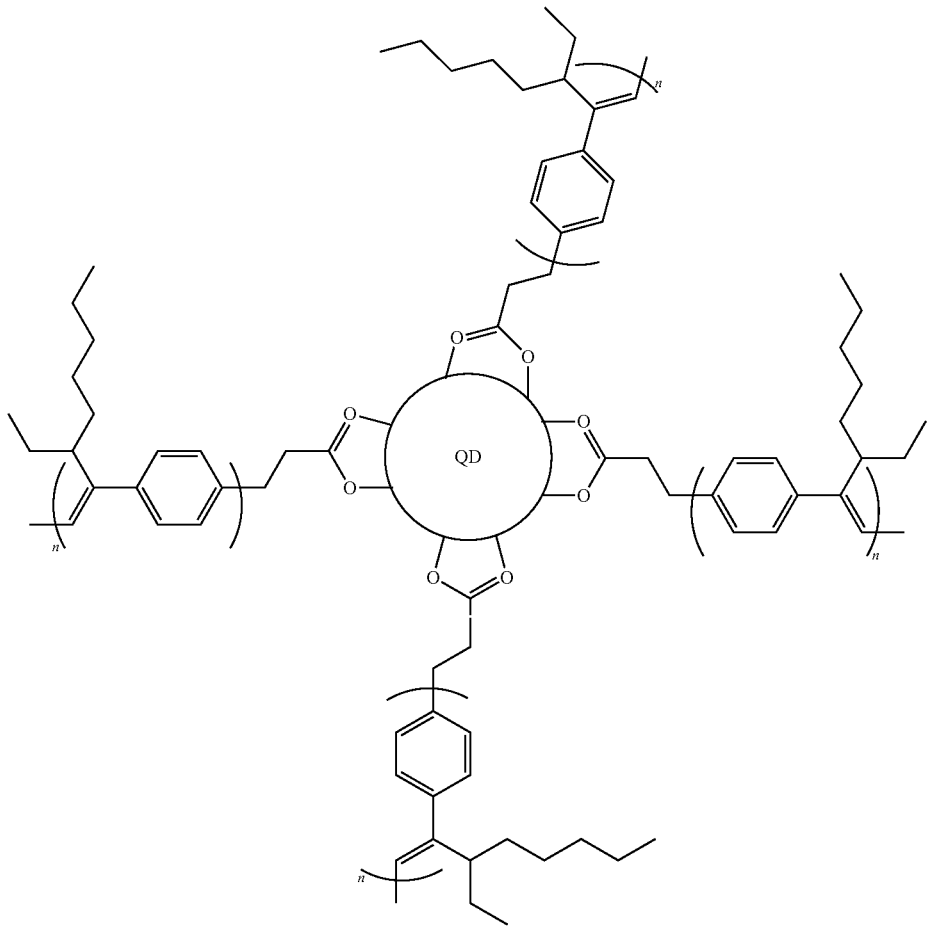

Formula (4)

Specifically, QD represents an inorganic part of the quantum dot structure, i.e., a quantum dot core structure or a core-shell structure. The organic ligands with a structural formula as Formula (2) are chelated on the QD. Through the carboxyl group of the organic ligand with a structure represented by Formula (2), the shell of the core-shell structure of the quantum dot and the organic ligand form a chelate linkage. Those skilled in the art can understand that the quantum dot structure materials, according to the fourth aspect of the present disclosure, are a detailed embodiment according to the second aspect of the present disclosure.

In the structure shown in Formula (4), the connection between the oxygen atoms of the organic ligands and a surface of the QD, shown as a surrounding circle, is represented by a covalent single bond connection. However, in some embodiments, such connection may be explained as having a complex connection mode.

Further, it can be understood that, the quantum dot structure materials according to the third aspect of the present disclosure have a small molecular structure, and the quantum dot structure materials according to the fourth aspect of the present disclosure have a macromolecular structure or a polymer structure.

A fifth aspect of the present disclosure provides a quantum-dot-containing layer. The quantum-dot-containing layer includes quantum dot structure materials disclosed according to any aspects from the second aspect to the fourth aspect of the present disclosure. The method for forming a quantum-dot-containing layer with quantum dot structure materials is not particularly limited. For example, a coating method may be applied, and a quantum-dot-containing layer may be formed by coating a surface of a plate with a solvent containing quantum dot structure materials.

A sixth aspect of the present disclosure provides a quantum-dot-based light emitting diode (QD-LED). The QD-LED includes the quantum-dot-containing layer according to the fifth aspect of the present disclosure. The method for producing the QD-LED is not particularly limited, and any method known in the art can be used to prepare the QD-LED.

Hereinafter, an exemplary method for preparing the QD organic ligand according to the first aspect of the present disclosure is described. A synthetic route according to principles of organic chemistry may be designed and applied to the preparation of the disclosed quantum dot organic ligand. The present disclosure provides chemical structure designs for QD organic ligands, that is, the R2 group having conjugated electron pair(s) are introduced in between the R1 group and the R3 group, to enhance the efficiency of quantum dots. Those skilled in the art, after having known the above principles, may understand the various methods of preparing the QD organic ligands according to the first aspect of the disclosure in accordance with the principles of organic chemistry.

As an example, R2 can have a condensed-ring aromatic hydrocarbon structure, also referred to as "polycyclic aromatic hydrocarbon structure", such as a pyrene structure. R1 and R3 can respectively bond to opposite positions, of opposite benzene rings, in the pyrene structure. Alternatively, R1 and R3 can respectively bond to non-opposing positions of opposite benzene rings in the pyrene structure. Further alternatively, R1 and R3 can even respectively bond to any positions of non-opposing benzene rings of the pyrene structure. According to different synthesis routes in organic chemistry, the various above-mentioned connections may be achieved.

In some embodiments, the method for preparing quantum dot organic ligands may include the following exemplary steps.

a) 2-bromopyrene is reacted with 1-bromooctane to produce 2-octylpyrene; b) the 2-octylpyrene is reacted with a brominating reagent to produce 9-bromo-2-octylpyrene; and c) 9-bromo-2-octylpyrene is reacted with a Grignard reagent for a Grignard reaction to produce 9-carboxy-2-octylpyrene. The produced quantum dot organic ligand has a structural formula as in Formula (1).

Formula (1)

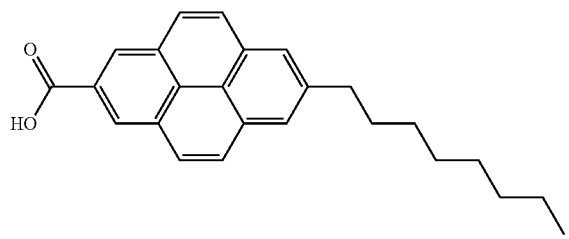

The specific synthetic route is as follows.

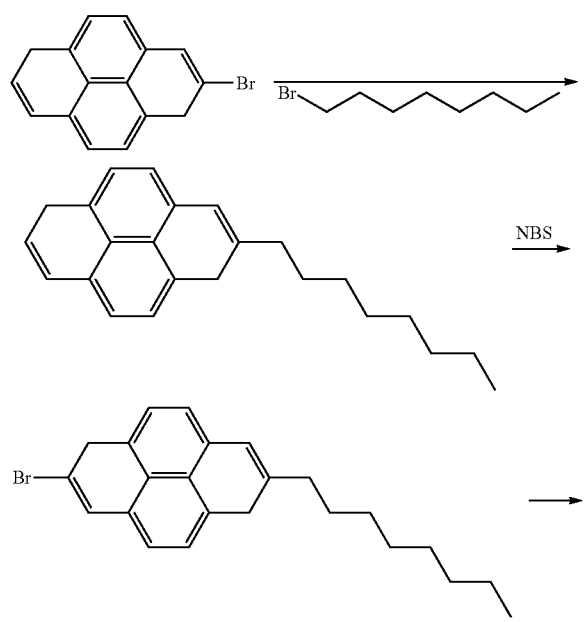

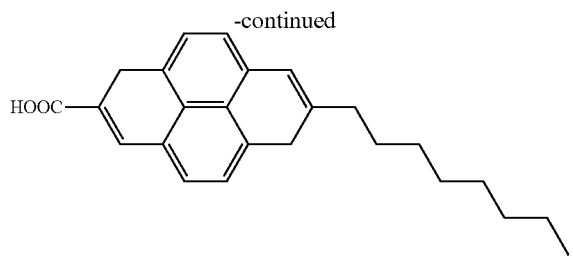

In the above synthetic route, NBS represents N-bromosuccinimide and is a brominating reagent. The brominating reagent, as used herein, may refer to a bromine-containing reagent capable of introducing a substitution reaction with a group having conjugated electron pair(s) such as a pyrene structure.

Specifically, the reaction procedure of step a) may include the following steps. The 2-bromopyrene is dissolved in dry ether, and then added with magnesium and iodine. The mixture is heated under reflux until the magnesium is dissolved completely. After being cooled down to room temperature, the mixture is added with 1-bromooctane, and is heated under reflux, so that the 2-bromopyrene reacts with the 1-bromooctane to produce a system containing 2-octylpyrene.

In one embodiment, after step a) and before step b), the preparation method may further include: purifying the system containing 2-octylpyrene to obtain 2-octylpyrene.

Further, the reaction procedure of step b) may include the following steps. The 2-octylpyrene is dissolved in chloroform, and added with acetic acid. The mixture is then added with N-bromosuccinimide as a brominating agent. The reaction may happen at room temperature to produce a system containing 9-bromo-2-octylpyrene.

In one embodiment, after step b) and before step c), the preparation method may further include: purifying the system containing 9-bromo-2-octylpyrene to obtain 9-bromo-2-octylpyrene.

Furthermore, the reaction procedure of step c) may include the following steps. The 9-bromo-2-octylpyrene is dissolved in dry ether, and then added with magnesium and iodine. The mixture is heated under reflux until the magnesium is dissolved completely. After being cooled down to room temperature, the reaction mixture is then poured into a container containing dry ice, and stirred until the temperature is raised to room temperature to obtain a system comprising 9-carboxy-2-octylpyrene.

In one embodiment, after step c), the preparation method may further include: purifying the system containing 9-carboxy-2-octylpyrene to obtain 9-carboxy-2-octylpyrene. The preparation method disclosed in these embodiments may be applied to synthesize small molecular type quantum dot organic ligands.

In some embodiments, the method for preparing quantum dot organic ligand may include the following steps.

1) 3-(bromomethyl)heptane is reacted with a dehydrobromination agent for a dehydrobromination reaction to produce 3-ethyl-1-octene; and 2) the 3-ethyl-1-octene, dibromobenzene, 3-(3-Bromophenyl)propionic acid, and a catalyst are dissolved in an organic solvent and heated for a reaction. The reaction is protected under an inert gas atmosphere to produce a polymer having the following structure:

Formula (2)

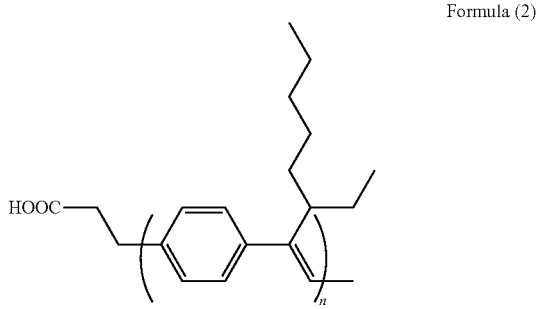

where n is an integer greater than 1.

The specific synthetic route is as follows.

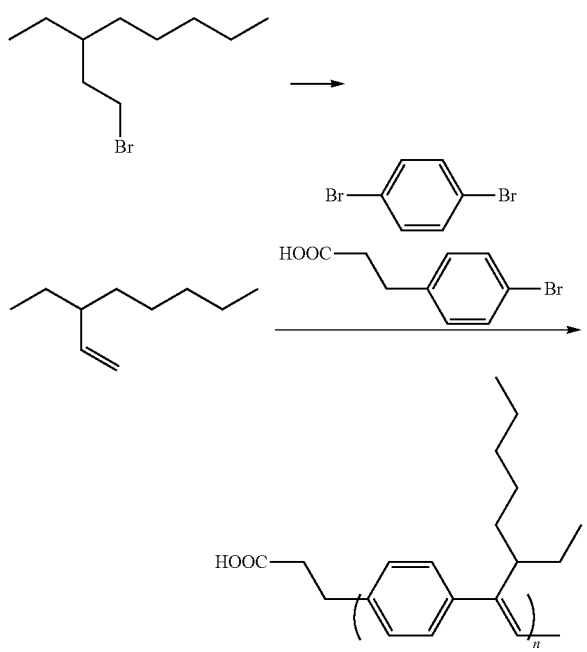

In the above synthetic route, the dehydrobromination reaction may be carried out in a basic environment, for example in the presence of NaOH. Specifically, the reaction procedure of step 1) may include the following steps. The 3-(bromomethyl)heptane is dissolved in ethanol, and added with NaOH for a reaction. The reaction is heated under reflux to obtain a mixture containing 3-ethyl-1-octene.

In one embodiment, after step a) and before step b), the following steps may be performed. The mixture is cooled down to room temperature, the ethanol may be removed by evaporation, and a purification method may be performed to obtain 3-ethyl-1-octene. For example, the purification method may be silica gel column chromatography.

In one embodiment, in step 1), the heat and reflux temperature may be 80° C. or higher, or even 85° C. or higher. In one embodiment, the catalyst in step 2) may be tetrakis(triphenylphosphine)palladium. In one embodiment, the inert gas in step 2) may be argon.

Further, the reaction procedure of step 2) may include the following steps. 3-ethyl-1-octene, 3-(3-Bromophenyl)propionic acid, and tetrakis(triphenylphosphine)palladium (i.e., chemical formula Pd(PPPh$_3$)$_4$) are dissolved in N, N'-dimethylformamide (i.e., DMF). Argon gas is introduced to remove oxygen. After that, the solution is heated for a reaction to obtain a mixture containing a polymer having a carboxyl group (abbreviated as PPV-COOH) as shown above.

In one embodiment, after step 2), the preparation method may further include: purifying the mixture containing PPV-COOH to obtain PPV-COOH. These embodiments may be applied to synthesize polymer type quantum dot organic ligands.

Following examples are provided to further describe the present disclosure.

Example 1: Preparation of Quantum Dot Organic Ligands 1) 2-bromopyrene (e.g., about 2.82 g) was dissolved in dry diethyl ether (e.g., about 100 mL), followed by adding magnesium ribbon (e.g., about 0.5 g) and iodine (e.g., about 0.1 g) therein. The mixture was heated to about 45° C. and the reaction was continued under reflux and maintained at the temperature until the magnesium ribbon was completely dissolved. The resulting mixture was cooled down to room temperature. Afterwards, the resulting mixture was added with 1-bromooctane (e.g., about 2 g), and heated under reflux, e.g., for about 12 hours, for a reaction. After the reaction, the reaction product was cooled down to room temperature. The solvent, diethyl ether, was removed from the reaction product by rotary evaporation. The reaction product was further purified using silica gel column chromatography to obtain 2-octylpyrene.

2) The 2-octylpyrene (e.g., about 1.86 g) was dissolved in chloroform (e.g., about 100 mL), and added with acetic acid (e.g., about 20 mL). N-bromosuccinimide (NBS) (e.g., about 9 g) was then added therein for a reaction at room temperature (e.g., for about 12 hours). After the reaction, water was added for extraction, where organic phase was collected and dried. The solvent, chloroform, was removed after drying. 9-bromo-2-octylpyrene was obtained after a silica gel column chromatography purification.

3) The 9-bromo-2-octylpyrene (e.g. about 0.9 g) was dissolved in dry diethyl ether (e.g., about 100 mL), followed by adding magnesium ribbon (e.g., about 0.15 g) and iodine (e.g., about 0.05 g) therein. The mixture was heated under reflux until the magnesium ribbon was completely dissolved. The resulting mixture was cooled down to room temperature. Afterwards, the resulting mixture was poured into a container containing dry ice (e.g., about 50 g), and stirred until the temperature of the reaction system was raised to room temperature. After the reaction, water was added for extraction, organic phase was collected and dried. The solvent, chloroform, was removed after drying. 9-carboxy-2-octylpyrene was obtained after a silica gel column chromatography purification.

The nuclear magnetic resonance (NMR) spectroscopy detection data of the quantum dot organic ligands prepared in Example 1 were as follows.

$^1$H NMR, dimethyl sulfoxide(DMSO)-d6, δ(ppm): 12.72 (1H, s), 8.90 (2H, s), 7.95 (6H, m), 2.75 (2H, t), 1.61 (2H, m), 1.23 (10H, m), 0.85 (3H, t).

Example 2: Preparation of Quantum Dot Structure Materials (Direct Method)

1) Te powder (e.g., about 0.01 g) and 9-carboxy-2-octylpyrene (e.g., about 0.054 g prepared according to Example 1) were dissolved in octadecene (e.g., about 2.5 mL) under a nitrogen atmosphere, so that Te stock solution were prepared.

2) CdO (e.g., about 0.015 g) and stearic acid (e.g., about 0.12 g) were placed in a three-necked flask, and added with octadecene (e.g., about 5 mL) under a nitrogen atmosphere. The reaction system was heated to 160° C. and stirred until complete dissolution of CdO. After the reaction system was cooled down to room temperature, hexadecylamine (HAD) (e.g., about 1.5 g) and 9-carboxy-2-octylpyrene (e.g., about 0.1 g prepared according to Example 1) were added to the reaction system. Under a nitrogen atmosphere, the reaction system was stirred and heated to about 290° C. After that, the Te stock solution obtained from step 1 was added quickly, and the reaction system was held at about 290° C. for about 60 minutes to let the quantum dot crystals grow. The reaction system was then rapidly cooled.

3) The reaction mixture obtained from the previous step was added with chloroform, and centrifuged to collect supernatant. The supernatant was added with methanol to precipitate the quantum dot structure materials. The lower sediment obtained from the centrifugation provides the quantum dot structure materials according to the third aspect of the present disclosure, which is a substance having a structure as Formula (3):

After drying, the quantum dot structure materials may be dissolved in hexane for preservation. Alternatively, the quantum dot structure materials may be dissolved in toluene.

The NMR detection data of the quantum dot structure materials prepared in Example 2 were as follows.

$^1$H NMR, (toluene)-d8, δ(ppm): 8.9 (21H), 7.9 (6H), 2.8 (2H), 1.6 (2H), 1.3 (10H), 0.8 (3H).

Example 3: Preparation of Quantum Dot Structure Materials (Ligand Exchange Method)

1) Te powder (e.g., about 0.01 g) and trioctylphosphine oxide (TOPO) (e.g., about 0.058 g) were dissolved in octadecene (e.g., about 2.5 mL) under a nitrogen atmosphere, so that Te stock solution were prepared.

2) CdO (e.g., about 0.015 g) and stearic acid (e.g., about 0.12 g) were placed in a three-necked flask, and added with octadecene (e.g., about 5 mL) under a nitrogen atmosphere. The reaction system was heated to 160° C. and stirred until complete dissolution of CdO. After the reaction system was cooled down to room temperature, HAD (e.g., about 1.5 g) and TOPO (e.g., about 0.1 g) were added to the reaction system. Under a nitrogen atmosphere, the reaction system was stirred and heated to about 290° C. After that, the Te stock solution obtained from step 1 was added quickly, and the reaction system was held at about 290° C. for about 60

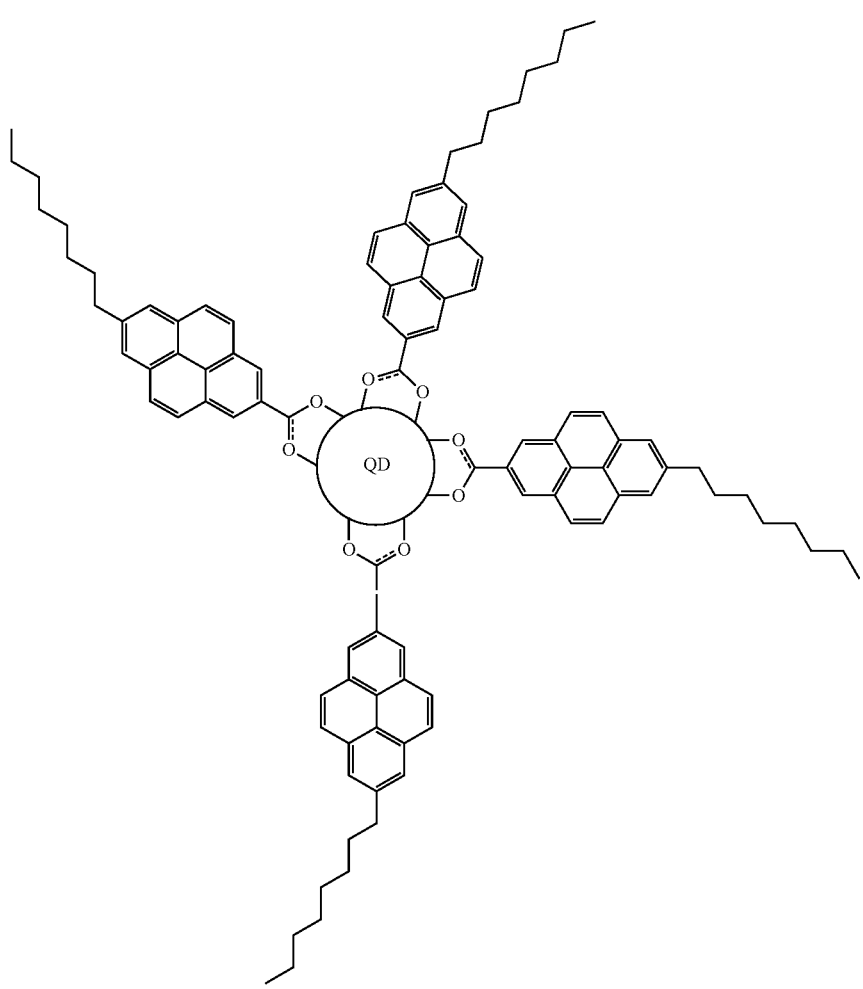

Formula (3)

minutes to let the quantum dot crystals grow. The reaction system was then rapidly cooled.

3) The reaction mixture was added with chloroform, and centrifuged to collect supernatant. The supernatant was added with methanol to precipitate the quantum dot structure materials. After the mixture went through centrifugation, the obtained lower sediments were CdTe quantum dot structure materials having TOPO as ligands.

4) The CdTe quantum dots having TOPO as ligands obtained from step 3 were added to pyridine (e.g., about 100 mL). After being stirred for 1 hour, the solution was concentrated (e.g., to about 10 mL) using a rotary evaporator. The concentrated solution was added with ethanol to precipitate the quantum dot structure materials. The precipitate was collected after centrifugation. At that time, the ligands of the quantum dot structure materials, TOPO, has been replaced with pyridine.

5) The precipitate obtained from step 4 was dissolved in toluene, and added with an excess amount of 9-carboxy-2-octylpyrene (e.g., the QD organic ligands prepared according to Example 1). After stirring the mixture for 1 hour, methanol was added to precipitate the quantum dot structure, the precipitated quantum dot structures having organic ligands that converted to the 9-carboxy-2-octyl-pyrene structure. After the mixture went through centrifugation, the obtained lower sediment is the quantum dot structure materials according to the third aspect of the present disclosure (e.g., having a structural formula as in Formula 3). After drying, the quantum dot structure materials containing 9-carboxy-2-octylpyrene may be dissolved in hexane for preservation. Alternatively, the quantum dot structure materials may be dissolved in toluene.

The NMR detection data of the quantum dot structure materials prepared in Example 3 were as follows.

$^1$H NMR, (toluene)-d8, δ(ppm): 8.9 (2H), 7.9 (6H), 2.8 (2H), 1.6 (2l1), 1.3 (10H), 0.8 (3H).

Example 4: Preparation of Quantum Dot Structure Materials (Ligand Exchange Method)

1) Te powder (e.g., about 0.01 g) and oleic acid (e.g., about 0.043 g) were dissolved in octadecene (e.g., about 2.5 mL) under a nitrogen atmosphere, so that Te stock solution were prepared.

2) CdO (e.g., about 0.015 g) and stearic acid (e.g., about 0.12 g) were placed in a three-necked flask, and added with octadecene (e.g., about 5 mL) under a nitrogen atmosphere. The reaction system was heated to 160° C. and stirred until complete dissolution of CdO. After the reaction system was cooled down to room temperature, HAD (e.g., about 1.5 g) and oleic acid (e.g., about 0.1 g) were added to the reaction system. Under a nitrogen atmosphere, the reaction system was stirred and heated to about 290° C. After that, the Te stock solution obtained from step 1 was added quickly, and the reaction system was held at about 290° C. for about 60 minutes to let the quantum dot crystals grow. The reaction system was then rapidly cooled.

3) The reaction mixture was added with chloroform, and centrifuged to collect supernatant. The supernatant was added with methanol to precipitate the quantum dot structure materials. The lower sediments obtained from the centrifugation provides the CdTe quantum dot structure materials having oleic acid as ligands.

4) The CdTe quantum dot structure materials having oleic acid as ligands obtained from step 3 were added to pyridine (e.g., about 100 mL). After being stirred for 1 hour, the solution was concentrated to about 10 mL using a rotary evaporator. After that, the solution was added with ethanol to let the quantum dot structure materials precipitate. The precipitate was collected after centrifugation. At that time, the ligands of the quantum dot structure materials, oleic acid, were replaced with pyridine.

5) The precipitate obtained from step 4 was dissolved in toluene, and added with an excess amount of 9-carboxy-2-octylpyrene (e.g., the QD organic ligands prepared according to Example 1). After stirring the mixture for 1 hour, methanol was added to precipitate the quantum dot structure materials, the precipitated quantum dot structure materials having organic ligands that converted to the 9-carboxy-2-octyl-pyrene structure. The lower sediment obtained from the centrifugation provides the quantum dot structure materials according to the third aspect of the present disclosure (e.g., having a structural formula in Formula 3). After drying, the quantum dot structure materials containing 9-carboxy-2-octylpyrene may be dissolved in hexane for preservation. Alternatively, the quantum dot structure materials may be dissolved in toluene.

The NMR detection data of the quantum dot structure materials prepared in Example 4 were as follows.

$^1$H NMR, (toluene)-d8, δ(ppm): 8.9 (2H), 7.9 (6H), 2.8 (2H), 1.6 (2H), 1.3 (10H), 0.8 (3H).

Example 5: Preparation of Quantum Dot Organic Ligand 1) 3-(bromomethyl)heptane (e.g., about 4.4 g) was dissolved in ethanol (e.g., about 100 mL), and added with NaOH. The mixture was heated until about 50-60° C. and the reaction was continued under reflux and maintained at the temperature, e.g., for about 12 hours. After the reaction, the reaction product was cooled down to room temperature. The ethanol was removed from the reaction product by rotary evaporation. The reaction product was further purified using silica gel column chromatography to obtain 3-ethyl-1-octene.

2) The 3-ethyl-1-octene (e.g., about 1 g), dibromobenzene (e.g., about 1.67 g), 3-(3-Bromophenyl)propionic acid (e.g., about 10 mg), and Pd(PPh$_3$)$_4$ (e.g., about 20 mg) were dissolved in N,N-dimethylformamide (DMF) (e.g., about 20 mL). After removing oxygen with argon gas, the solution was heated to 90° C. for a reaction (e.g., for about 24 hours). After the reaction, the solution was diluted with tetrahydrofuran. The catalyst was removed by neutral alumina column chromatography. Further, the solution was concentrated (e.g., to about 10 mL) using a rotary evaporator. The concentrated solution was added with methanol to precipitate the quantum dot structure materials. The resultant was dried to give quantum dot organic ligands with a structure shown as Formula (2).

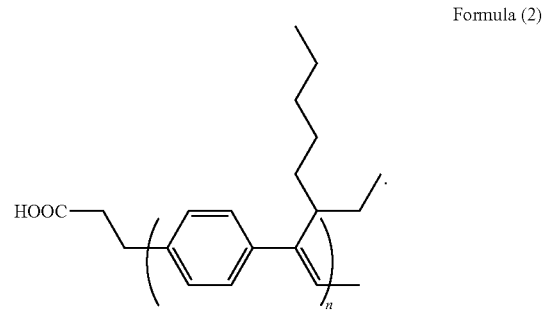

Formula (2)

The NMR spectroscopy detection data of the quantum dot organic ligands prepared in Example 5 were as follows.

$^1$H NMR, DMSO-d6, δ(ppm): 6.77-6.94 (4H), 5.80 (1H), 2.76 (2H), 2.00 (2H), 1.25-1.42 (10H), 0.96 (3H).

Example 6: Preparation of Quantum Dot Structure Materials (Ligand Exchange Method)

1) Te powder (e.g., about 0.01 g) and TOPO (e.g., about 0.058 g) were dissolved in octadecene (e.g., about 2.5 mL) under a nitrogen atmosphere, so that Te stock solution were prepared.

2) CdO (e.g., about 0.015 g) and stearic acid (e.g., about 0.12 g) were placed in a three-necked flask, and added with octadecene (e.g., about 5 mL) under a nitrogen atmosphere. The reaction system was heated to 160° C. and stirred until complete dissolution of CdO. After the reaction system was cooled down to room temperature, HAD (e.g., about 1.5 g) and TOPO (e.g., about 0.1 g) were added to the reaction system. Under a nitrogen atmosphere, the reaction system was stirred and heated to about 290° C. After that, the Te stock solution obtained from step 1 was added quickly, and the reaction system was held at about 290° C. for about 60 minutes to let the quantum dot crystals grow. The reaction system was then rapidly cooled.

3) The reaction mixture was added with chloroform, and centrifuged to collect supernatant. The supernatant was added with methanol to precipitate the quantum dot structure materials. The lower sediments obtained from the centrifugation provides the CdTe quantum dot structure materials having TOPO as ligands.

4) The CdTe quantum dot structure materials having TOPO as ligands obtained from step 3 were added to pyridine (e.g., about 100 mL). After being stirred for 1 hour, the solution was concentrated (e.g., to about 10 mL) using a rotary evaporator. The concentrated solution was added with ethanol to precipitate the quantum dot structure materials. The precipitate was collected after centrifugation. At that time, the ligands of the quantum dot structure materials, TOPO, has been replaced with pyridine.

5) The precipitate obtained from step 4 was dissolved in toluene, and added with an excess amount of the QD organic ligands prepared according to Example 5. After being stirred for about 1 hour, the mixture was added with methanol to let the quantum dot structure materials precipitate, the precipitated quantum dot structure materials having organic ligands that converted to the structure according to Example 5. After the mixture went through centrifugation, the obtained lower sediment is the quantum dot structure materials according to the fourth aspect of the present disclosure. The quantum dot structure materials had a structural formula as Formula (4).

Formula (4)

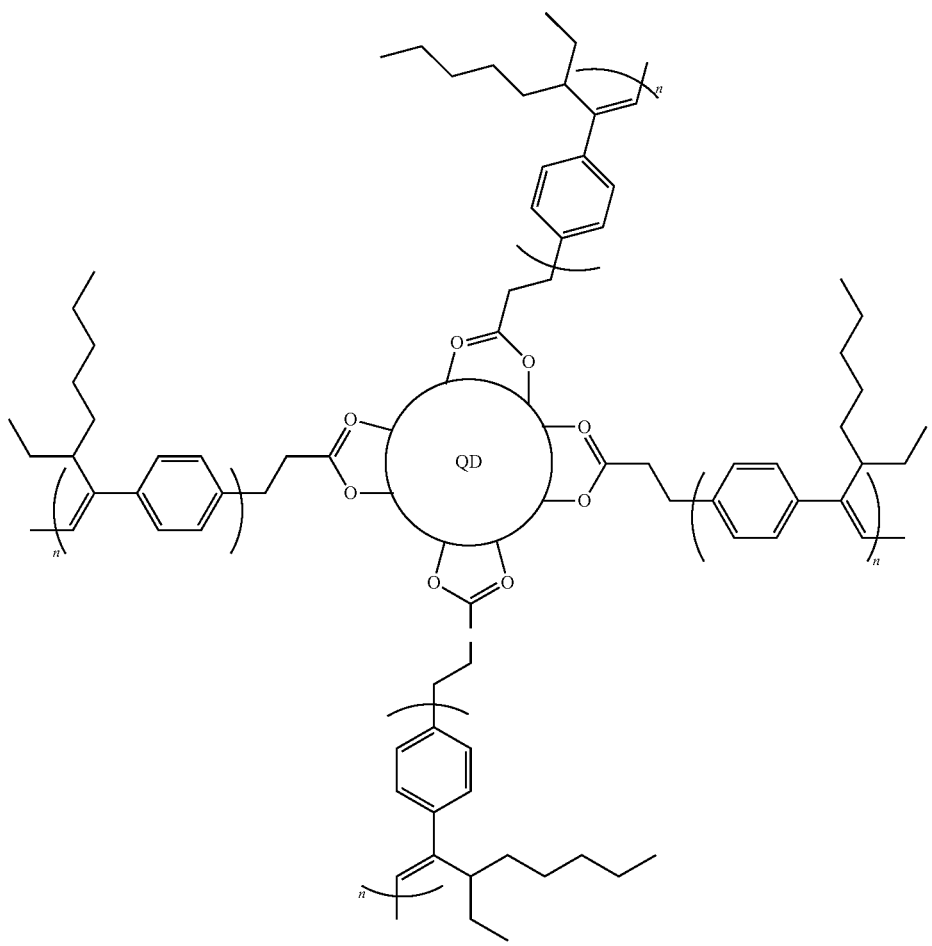

After drying, the quantum dot structure materials may be dissolved in hexane for preservation. Alternatively, the quantum dot structure materials may be dissolved in toluene.

Example 7: Preparation of Quantum Dot Structure Materials (Ligand Exchange Method)

1) Te powder (e.g., about 0.01 g) and oleic acid (e.g., about 0.043 g) were dissolved in octadecene (e.g., about 2.5 mL) under a nitrogen atmosphere, so that Te stock solution were prepared.

2) CdO (e.g., about 0.015 g) and stearic acid (e.g., about 0.12 g) were placed in a three-necked flask, and added with octadecene (e.g., about 5 mL) under a nitrogen atmosphere. The reaction system was heated to 160° C. and stirred until complete dissolution of CdO. After the reaction system was cooled down to room temperature, HAD (e.g., about 1.5 g) and oleic acid (e.g., about 0.1 g) were added to the reaction system. Under a nitrogen atmosphere, the reaction system was stirred and heated to about 290° C. After that, the Te stock solution obtained from step 1 was added quickly, and the reaction system was held at about 290° C. for about 60 minutes to let the quantum dot crystals grow. The reaction system was then rapidly cooled.

3) The reaction mixture was added with chloroform, and centrifuged to collect supernatant. The supernatant was added with methanol to precipitate the quantum dot structure materials. The lower sediments obtained from the centrifugation provides CdTe quantum dot structure materials having oleic acid as ligands.

4) The CdTe quantum dot structure materials having oleic acid as ligands obtained from step 3 were added to pyridine (e.g., about 100 mL). After being stirred for 1 hour, the solution was concentrated to about 10 mL using a rotary evaporator. After that, the solution was added with ethanol to let the quantum dot structure materials precipitate. The precipitate was collected after centrifugation. At that time, the ligands of the quantum dot structure materials, TOPO, has been replaced with pyridine.

5) The precipitate obtained from step 4 was dissolved in toluene, and added with an excess amount of the QD organic ligands prepared according to Example 5. After being stirred for about 1 hour, the mixture was added with methanol to precipitate the quantum dot structure materials, the precipitated quantum dot structure materials having organic ligands that converted to the structure according to Example 5. After the mixture went through centrifugation, the obtained lower sediment is the quantum dot structure materials according to the fourth aspect of the present disclosure. The quantum dot structure materials had a structural formula as Formula (4).

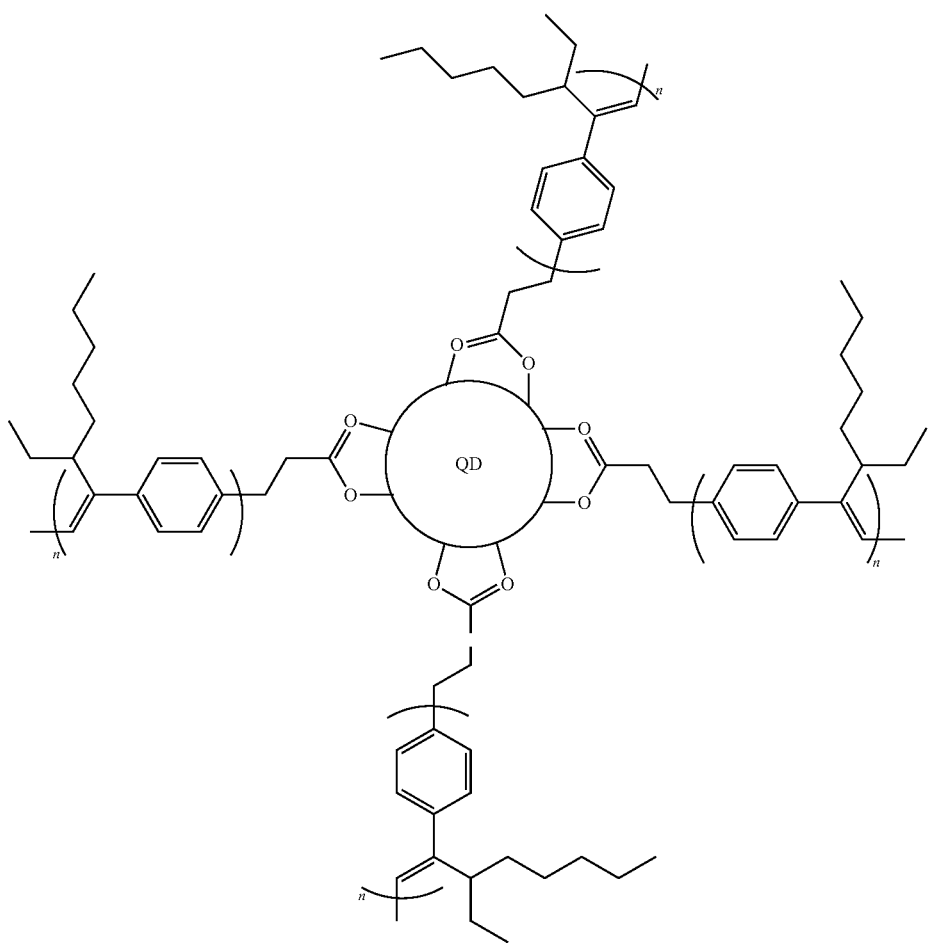

Formula (4)

After drying, the quantum dot structure materials may be dissolved in hexane for preservation. Alternatively, the quantum dot structure materials may be dissolved in toluene.

Further, spectral analysis was performed on the CdTe QDs with oleic acid as ligands obtained from step 3 of Example 7, QDs having a structure as Formula (4) obtained according to step 5 of Example 7, and quantum dot organic ligands obtained according to Example 5. Their UV-visible absorbance spectra and photoluminescence emission spectra are respectively illustrated in FIG. 1 and FIG. 2.

Figure 2:
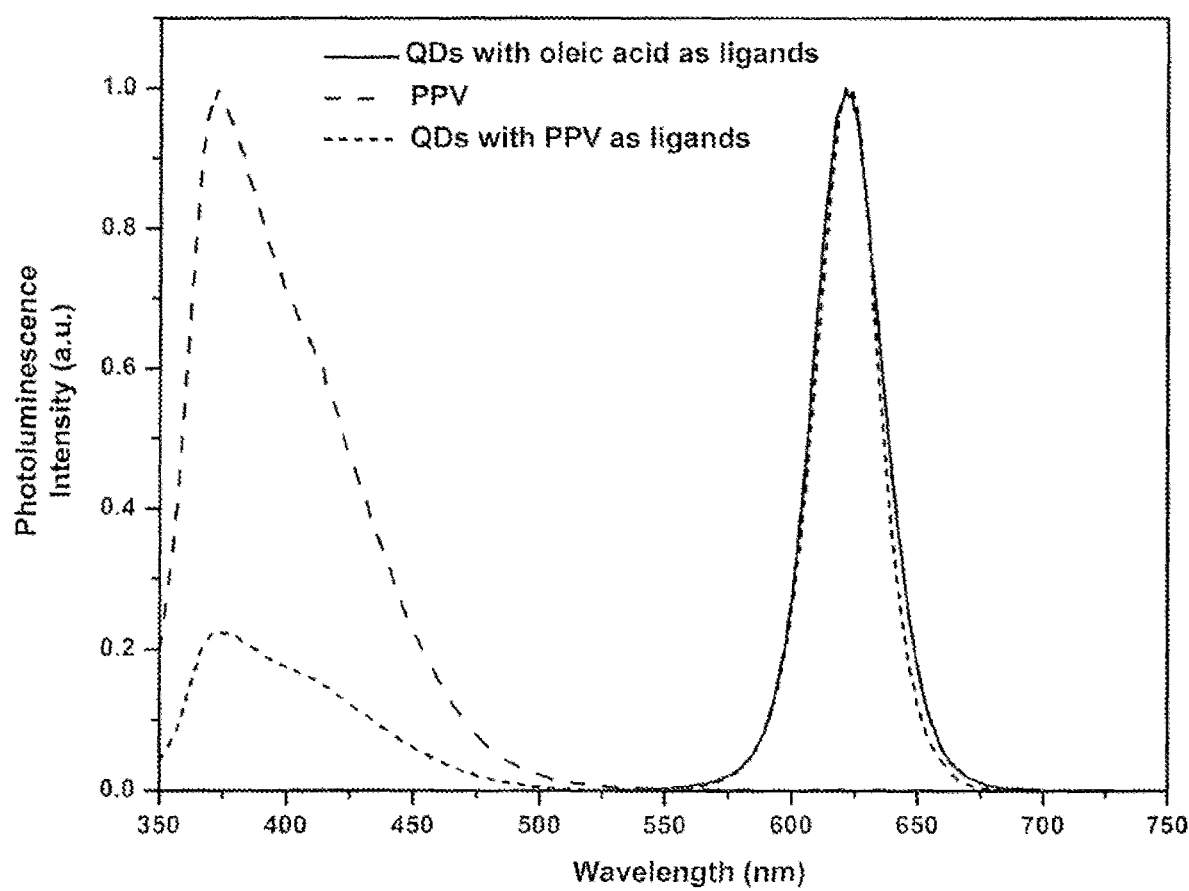
FIG. 2 is a comparison chart illustrating photoluminescence emission spectra of: CdTe QDs with oleic acid as ligands prepared according to step 3 of Example 7, QDs with a structural formula as Formula (4) prepared according to step 5 of Example 7, and QD organic ligands prepared according to Example 5.

In FIGS. 1-2, a solid line represents QD materials with oleic acid as ligands, a dashed line represents PPV, and a dotted line represents QD materials with PPV as ligands. Specifically, the solid line illustrates the spectrum of the CdTe QDs with oleic acid as ligands obtained according to step 3 of Example 7; the dotted line illustrates the spectrum of the QDs with a structure as Formula (4) obtained according to step 5 of Example 7; and the dashed line illustrates the spectrum of the QD organic ligands prepared according to Example 5, PPV, as used in the figures, may refer to the quantum dot organic ligand with a structural formula as Formula (2).

As shown in FIGS. 1-2, the QD materials with PPV as ligands may include spectrum features from PPV and the QD. The UV-visible absorption spectra and the fluorescence emission spectra both demonstrate that the PPV ligands are successfully attached to QDs. This in turn provides evidences of successful completion of the ligand exchange in Example 7.

Examples 8-12: Preparation of QD-LEDs

The method for preparing QD-LED may include the following exemplary steps.

1) Cleaning a Glass Substrate Containing a Nano ITO Transparent Electrode (i.e., Anode)

Specifically, the glass substrate containing a nano ITO transparent electrode was continuously sonicated (e.g., for about 15 minutes) using deionized water and isopropanol respectively. After being quickly blown dry with a nitrogen gun, the glass substrate was baked (e.g., for about 5 minutes) on a hot plate (e.g., at a temperature of 150° C.). After that, the glass substrate was treated with UV light and ozone (e.g., for about half an hour), so that the surface of ITO transparent electrode became clean, and the work function of the ITO electrode can be improved.

2) Preparation of Hole Injection Layer

In air atmosphere, PEDOT:PSS (i.e., poly(3,4-ethylenedioxythiophene) polystyrene sulfonate) was spin-coated on the cleaned glass substrate at a speed of about 3000 rpm for about 1 minute. When the spin-coating was finished, the glass substrate was annealed in air at about 130° C. for 20 minutes, and the solvent that not volatized was dried. The glass substrate was then transferred to an argon glove box.

3) Preparation of Hole Transport Layer

In the argon glove box, a toluene solvent of poly(N-vinylcarbazole) (PVK) were spin-coated on the PEDOT:PSS film. The revolution speed was about 2500 rpm, and the spin-coating time duration was about 45 seconds. After the spin-coating was completed, the glass substrate was annealed in the glove box at about 120° C. for about 20 minutes.

4) Preparation of Light-Emitting Layer

The hexane solution containing QDs obtained according to any of Examples 2-4 and 6-7 (e.g., at a concentration of about 30 mg/mL) was spin-coated on the PVK film. The spin coating time duration was about 45 seconds. After the spin-coating was completed, the glass substrate was annealed in the glove box at about 130° C. for about 30 minutes.

5) Preparation of Electron Injection Layer

An ethanol solution containing ZnO nanoparticles (e.g., at a concentration of about 30 mg/mL) was spin-coated on the previously-formed quantum dot light emitting layer (e.g., at a speed of 1500 rpm for about 45 seconds), thus forming the electron injection layer. Particle size of the ZnO nanoparticles is at most 5 nm.

6) Cathode Vapor Deposition

After the spin-coating was completed, the device was placed in a vacuum deposition chamber, to deposit aluminum cathode with a deposition thickness of about 200 nm. A light emitting diode was then obtained.

The QD-LEDs prepared according to Examples 8-12 respectively contain quantum dot structure materials prepared according to Examples 2-4 and 6-7.

Example 13: Structure of a QD-LED

Figure 3:
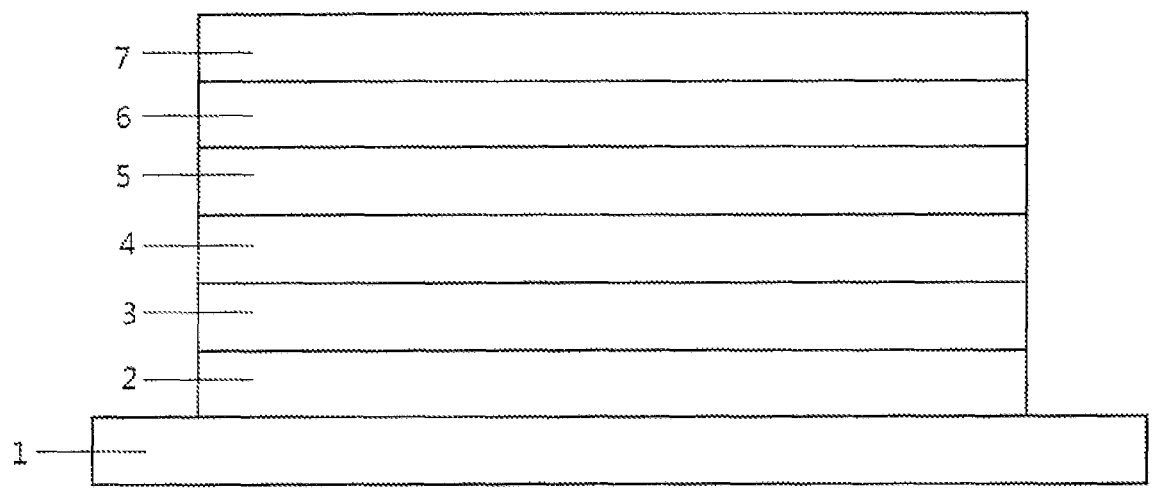
FIG. 3 is a structure diagram illustrating an exemplary QD-LED according to various embodiments of the present disclosure.

This example provides a structure of a QD-LED. FIG. 3 is a structure diagram illustrating an exemplary QD-LED according to various embodiments of the present disclosure. As shown in FIG. 3, the disclosed QD-LED may include, from bottom to top in sequence: a glass substrate 1, an ITO electrode 2 formed on the surface of the glass substrate 1, a hole injection layer 3, a hole transport layer 4, a light-emitting layer 5, an electron injection layer 6, and an aluminum layer 7. The QD-LED in this example may be prepared according to Examples 8-12. The glass substrate 1 and the ITO electrode 2 may use existing glass substrate containing transparent ITO electrode.

Figure 4:
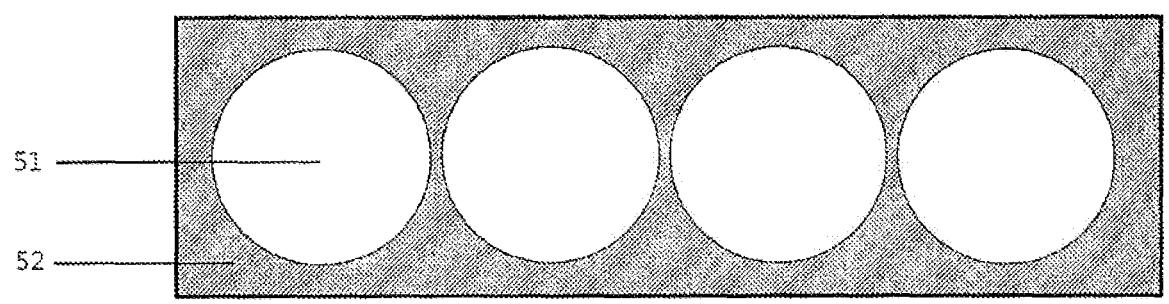
FIG. 4 is a schematic view illustrating an internal structure of an exemplary light-emitting layer according to various embodiments of the present disclosure.

As shown in FIG. 4, it is generally believed in the art that the light emitting-layer 5 include QD core-shells 51 and QD organic ligands 52. FIG. 4 is a schematic view illustrating an internal structure of the light-emitting layer 5. The actual internal structure may be more complex than that shown in FIG. 4. For example, the QD core-shells 51 and the QD organic ligands 52 may be cluttered and mutually staggered.

Figure 5A:
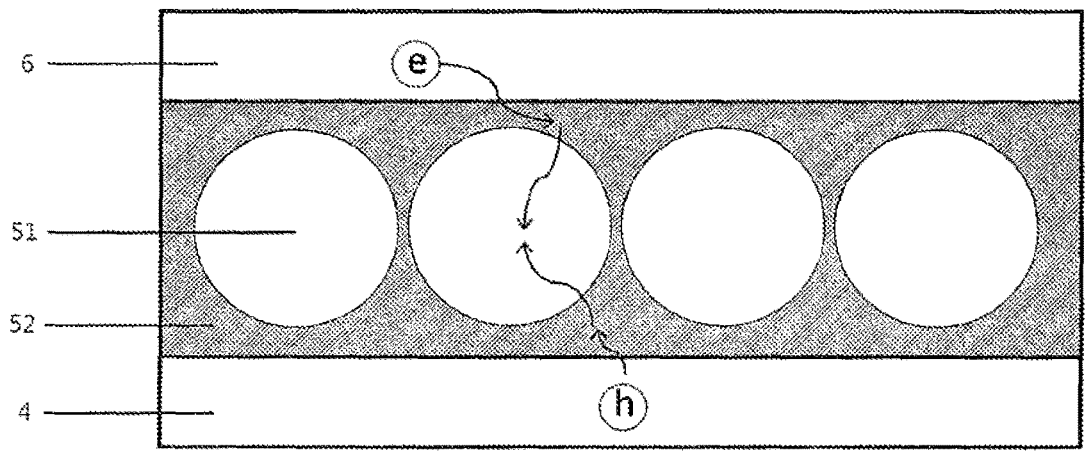
FIG. 5a is a diagram illustrating an exemplary working principle of QD-LED according to various embodiments of the present disclosure.
Figure 5B:
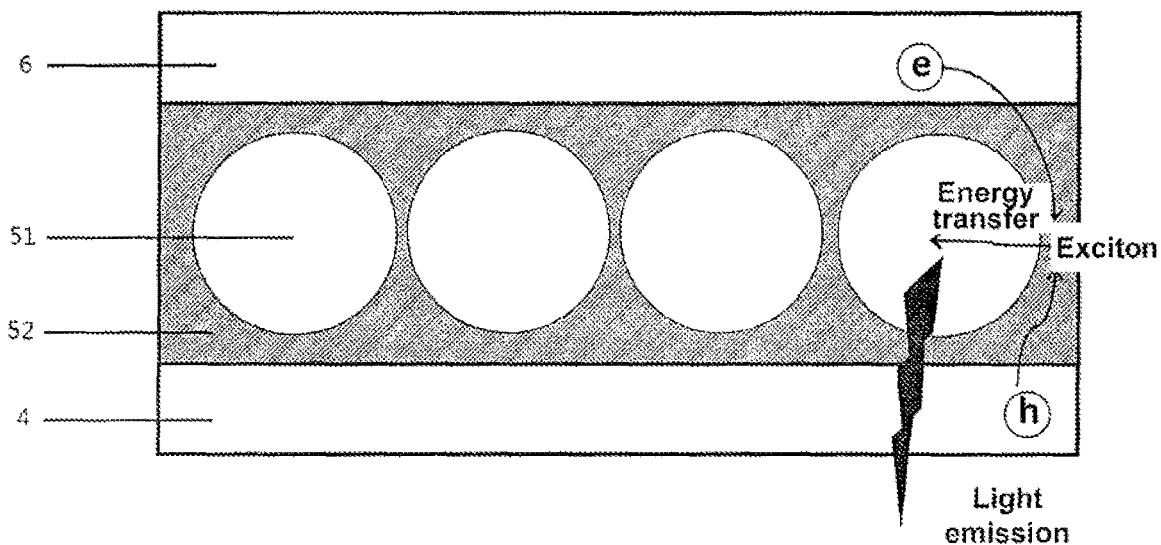
FIG. 5b is a diagram illustrating another exemplary working principle of QD-LED according to various embodiments of the present disclosure.

The QD-LEDs provided in the present disclosure may have two working principles, which are respectively shown in FIG. 5a and FIG. 5b. FIG. 5a is a diagram illustrating an exemplary working principle of QD-LED according to various embodiments of the present disclosure; and FIG. 5b is a diagram illustrating another exemplary working principle of QD-LED according to various embodiments of the present disclosure.

In FIG. 5a, the QD organic ligands 52 have conjugated electron pairs, leading to the occurrence of typical electron delocalization effects, which can improve the electron/hole transport. In FIG. 5a, a hole h and an electron e can easily move through the QD organic ligands 52 to the core-shell structure 51 so that the hole h or the electron e may be further transported/conducted.

In FIG. 5b, the QD organic ligand 52 itself is a conjugated luminescent functional group. According to the mechanism of Förster energy transfer, electrons e and holes h may form an exciton in the QD organic ligand 52, the exciton transfers energy to the QD core-shell 51, and then photons are emitted. In this way, the problem that difficult injection of holes/electrons into QD core-shell may be avoided. On the other hand, since the ligand and the QD core-shell are connected by chemical bonds, it is much easier for the exciton to transfer energy.

According to the above two interpretations, the structure of quantum dot structure materials containing the organic ligands as disclosed in various embodiments of the present disclosure may improve the utilization of electrons and/or holes, which ultimately improves the efficiency of light-emitting diodes, and can also reduce the turn-on voltage.

Testing results shown that, compared to QDs without conjugated electron pairs in the prior art, the light emitting diodes prepared according to Examples 8-12 have increased efficiency and decreased turn-on voltage. It should be noted that, the test methods from CIE 127-1997 "Measurement of LEDs" were applied to test the efficiency of the LEDs. Specifically, external quantum efficiency was measured. In addition, the turn-on voltage, or the light-up voltage, as used herein, refer to the voltage when the brightness of the QD-LED reaches 1 cd/m².

Other embodiments of the disclosure will be apparent to those skilled in the art from consideration of the specification and practice of the disclosure disclosed herein. It is intended that the specification and examples be considered as exemplary only, with a true scope and spirit of the disclosure being indicated by the claims.

What is claimed is:

1. A quantum dot organic ligand, comprising a structure represented by a formula selected from a group consisting of:

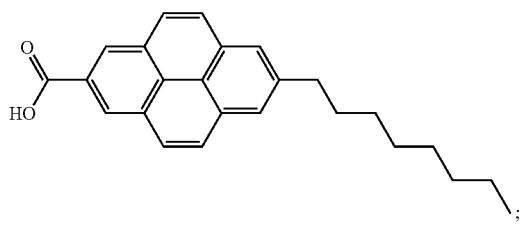 [SMILES: CCCCCCCCc1cc2ccc3cc(C(=O)O)cc4ccc(c1)c2c34]

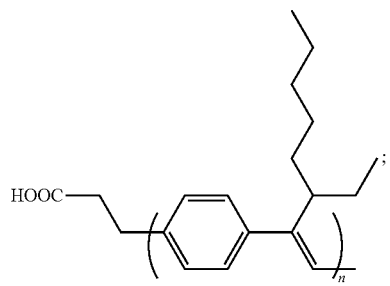

and

R1-(R2-R3)$_n$, wherein R1 is a chelating group capable of chelating with a metal, R2 comprises a structure selected from the group consisting of a 9, 10-di(2-naphthyl)anthracene structure, a rubrene structure, and a combination thereof, R3 is an organic group connected to R2;

wherein n is a positive integer.

2. The quantum dot organic ligand according to claim 1, wherein R1 comprises a group selected from the group consisting of a phosphine group, a phosphonic acid group, an amino group, a mercapto group, a hydroxyl group, and a combination thereof.

3. The quantum dot organic ligand according to claim 1, wherein R3 comprises an alkane group.

4. A quantum dot structure, comprising:
the quantum dot organic ligand according to claim 1 in chelated form; and
a core or a core-shell;
wherein the quantum dot organic ligand is chelated to the core, or to a shell part of the core-shell.

5. The quantum dot structure of claim 4, comprising a structure represented by Formula (3):

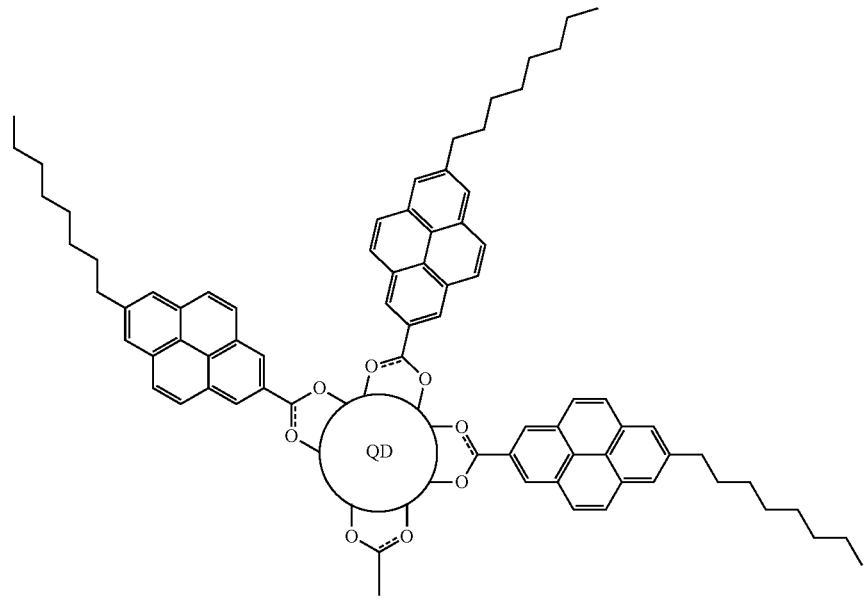

Formula (3)

-continued

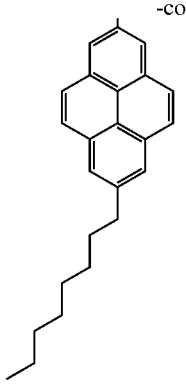

wherein:
QD is an inorganic part of the quantum dot structure, comprising the core or the core-shell.

6. The quantum dot structure according to claim 5, wherein the inorganic part of the quantum dot structure is made of one or more materials selected from CdS, CdSe, CdTe, ZnSe, InP, PbS, $CsPbCl_3$, $CsPbBr_3$, $CsPhI_3$, $CsPbCl_xBr_{3-x}$, $CsPbBr_xI_{3-x}$, CdS/ZnS, CdSe/ZnS, ZnSe, InP/ZnS, PbS/ZnS, $CsPbCl_3$/ZnS, $CsPbBr_3$/ZnS, $CsPhI_3$/ZnS, $CsPbClxBr_{3-x}$/ZnS, $CsPbBrxI_{3-x}$/ZnS, or a combination thereof, wherein x is a positive integer and x<3.

7. The quantum dot structure of claim 4, comprising a structure represented by Formula (4)

wherein:
QD represents an inorganic part of the quantum dot structure, comprising the core or the core-shell.

8. The quantum dot structure according to claim 7, wherein the inorganic part of the quantum dot structure is made of one or more materials selected from CdS, CdSe, CdTe, ZnSe, InP, PbS, $CsPbCl_3$, $CsPbBr_3$, $CsPhI_3$, $CsPbCl_xBr_{3-x}$, $CsPbBr_xI_{3-x}$, CdS/ZnS, CdSe/ZnS, ZnSe, InP/ZnS, PbS/ZnS, $CsPbCl_3$/ZnS, $CsPbBr_3$/ZnS, $CsPhI_3$/ZnS, $CsPbClxBr_{3-x}$/ZnS, $CsPbBrxI_{3-x}$/ZnS, or a combination thereof, wherein x is a positive integer and x<3.

9. A quantum-dot-containing layer, comprising the quantum dot structure according to claim 4.

Formula (4)

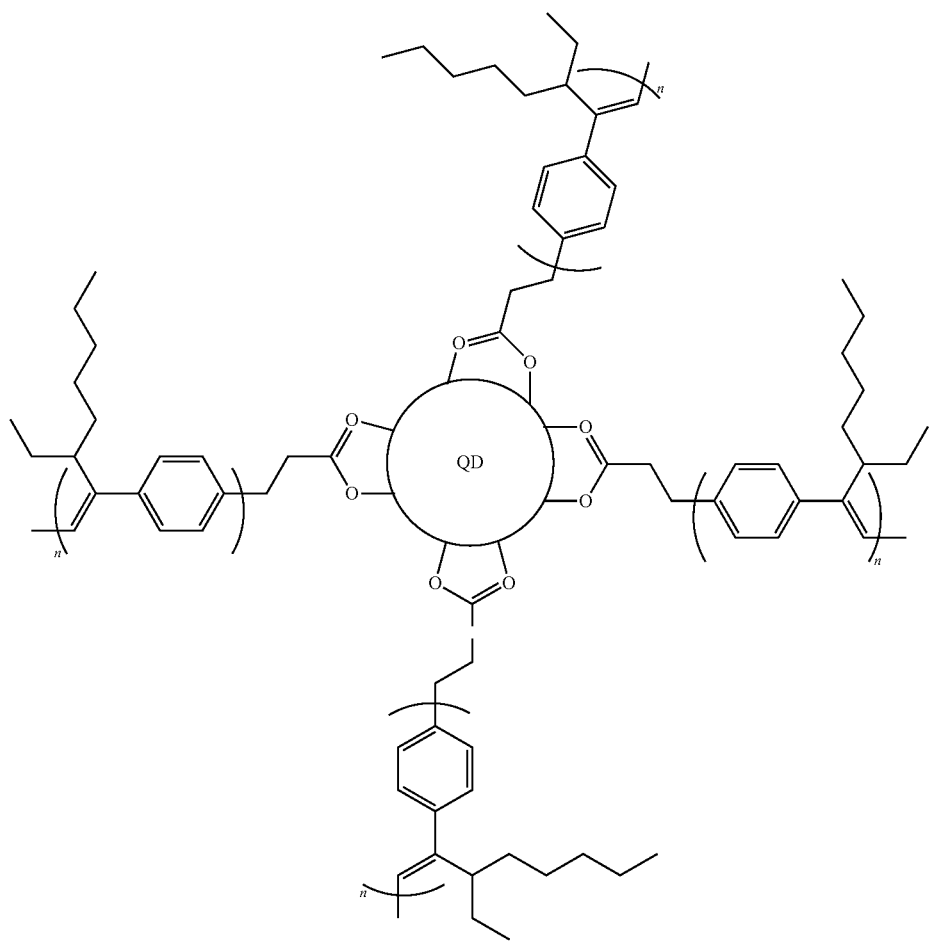

10. A quantum-dot-based light emitting diode, comprising a quantum-dot-containing layer according to claim 9.

\* \* \* \* \*